United States Patent
Smalley et al.

(10) Patent No.: US 7,074,310 B2
(45) Date of Patent: Jul. 11, 2006

(54) METHOD FOR SEPARATING SINGLE-WALL CARBON NANOTUBES AND COMPOSITIONS THEREOF

(75) Inventors: Richard E. Smalley, Houston, TX (US); Robert H. Hauge, Houston, TX (US); W. Carter Kittrell, Houston, TX (US); Ramesh Sivarajan, Houston, TX (US); Michael S. Strano, Champaign, IL (US); Sergei M. Bachilo, Houston, TX (US); R. Bruce Weisman, Houston, TX (US)

(73) Assignee: William Marsh Rice University, Houston, TX (US)

( * ) Notice: Subject to any disclaimer, the term of this patent is extended or adjusted under 35 U.S.C. 154(b) by 629 days.

(21) Appl. No.: 10/379,273

(22) Filed: Mar. 4, 2003

(65) Prior Publication Data

US 2004/0040834 A1    Mar. 4, 2004

Related U.S. Application Data

(60) Provisional application No. 60/390,887, filed on Jun. 24, 2002, provisional application No. 60/361,594, filed on Mar. 4, 2002, provisional application No. 60/361,593, filed on Mar. 4, 2002.

(51) Int. Cl.
*G01N 27/447* (2006.01)
*B03C 5/00* (2006.01)
*B01D 15/08* (2006.01)

(52) U.S. Cl. ............... 204/450; 204/451; 204/456; 210/656; 210/748

(58) Field of Classification Search ........ 204/600–613, 204/616–618, 450–461, 466, 467; 210/656, 210/748
See application file for complete search history.

(56) References Cited

U.S. PATENT DOCUMENTS 6,183,714 B1    2/2001    Smalley et al. .......... 423/447.3

(Continued)

FOREIGN PATENT DOCUMENTS

WO    WO 00/26138    5/2000

(Continued)

OTHER PUBLICATIONS

JPO English language computer translation of Hidefumi (JP 08-231210 A), Sep. 10, 1996.*

(Continued)

*Primary Examiner*—Alex Noguerola
(74) *Attorney, Agent, or Firm*—Ross Spencer Garsson; Edward T. Mickelson; Winstead Sechrest & Minick P.C.

(57) ABSTRACT

The invention relates to a process for sorting and separating a mixture of (n, m) type single-wall carbon nanotubes according to (n, m) type. A mixture of (n, m) type single-wall carbon nanotubes is suspended such that the single-wall carbon nanotubes are individually dispersed. The nanotube suspension can be done in a surfactant-water solution and the surfactant surrounding the nanotubes keeps the nanotube isolated and from aggregating with other nanotubes. The nanotube suspension is acidified to protonate a fraction of the nanotubes. An electric field is applied and the protonated nanotubes migrate in the electric fields at different rates dependent on their (n, m) type. Fractions of nanotubes are collected at different fractionation times. The process of protonation, applying an electric field, and fractionation is repeated at increasingly higher pH to separated the (n, m) nanotube mixture into individual (n, m) nanotube fractions. The separation enables new electronic devices requiring selected (n, m) nanotube types.

62 Claims, 21 Drawing Sheets

U.S. PATENT DOCUMENTS 6,683,783 B1 * 1/2004 Smalley et al. ............. 361/502
2003/0168385 A1 * 9/2003 Papadimitrakopoulos ...... 209/1

FOREIGN PATENT DOCUMENTS

WO     WO 02/16257 A2    2/2002
WO     WO 02/079082 A2    10/2002

OTHER PUBLICATIONS

Collins, Philip G. "Extreme Oxygen Sensitivity of Electronic Properties of Carbon Nanotubes," *Science*, Mar. 10, 2000, vol. 287, pp. 1801-1804.

Kong, Jing. "Nanotube Molecular Wires as Chemical Sensors," *Science*, Jan. 28, 2000, vol. 287, pp. 622-625.

Lee, R.S. "Conductivity Enhancement in Single-Walled Carbon Nanotube Bundles Doped with K and Br," *Nature*, Jul. 17, 1997, vol. 88, pp. 255-257.

Bachilo et al., "Structure-Assigned Optical Spectra of Single-Walled Carbon Nanotubes," *Science*, vol. 298, pp. 2361-2365 (Dec. 20, 2002).

Dresselhaus et al., "$C_{60}$-Related Tubules and Spherules," *Science of Fullerenes and Carbon Nanotubes*, Chapter 19, Academic Press, San Diego, pp. 756-869 (1996).

O'Connell et al., "Reversible Water Solubilization of Single-Walled Carbon Nanotubes by Polymer-Wrapping," *Chemical Physics Letters*, vol. 342, pp. 265-271 (Jul. 13, 2001).

Yakobson et al., "Fullerene Nanotubes: $C_{1,000,000}$ and Beyond," *American Scientist*, vol. 85, pp. 324-337 (Jul.-Aug. 1997).

* cited by examiner

First Injection pH = 8.8

Starting Solution

HPR87 1% SDS/D2O

Prepared 12-3-01

Concentration ~ 20 mg/L, 15 ml starting vol.
pH corrected to 10.3 using 0.1 N NaOH Injected 10 µl of 0.1 N HCl
Minor decrease in quantum yield
and RBM intensity

Third Injection
pH = 5.98

Injected 10 μl of 0.1 N HCl
Minor decrease in quantum yield and RBM intensity

Second Injection
pH = 6.63

Injected 10 μl of 0.1 N HCl
Buffering effect: 6.6 → 4.4 → 6.0
1022, 1034 and 1055 nm VHS are quenching

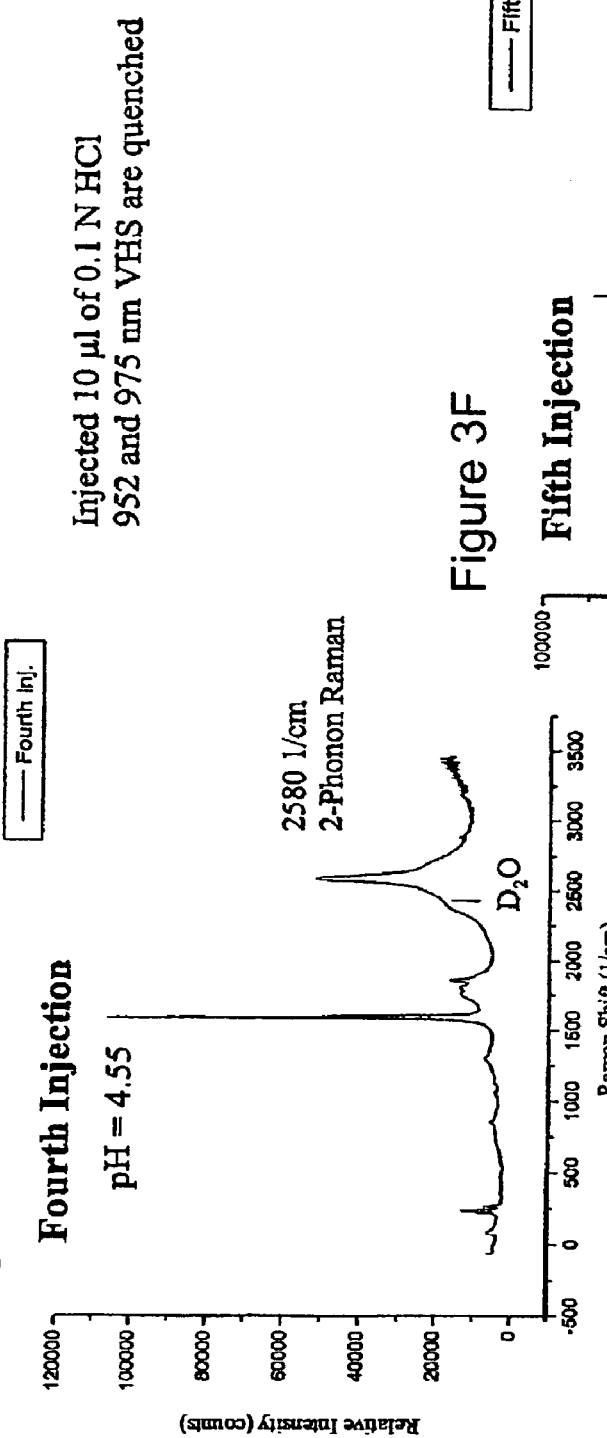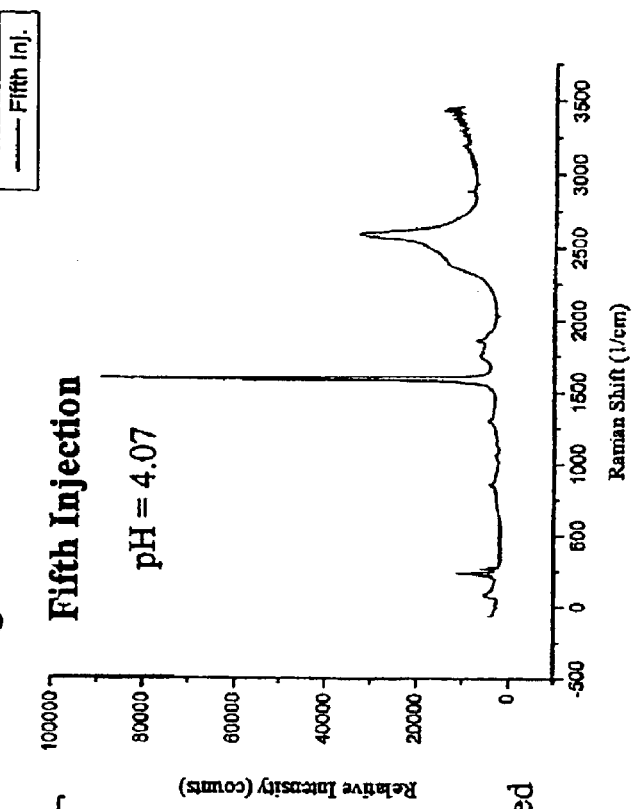

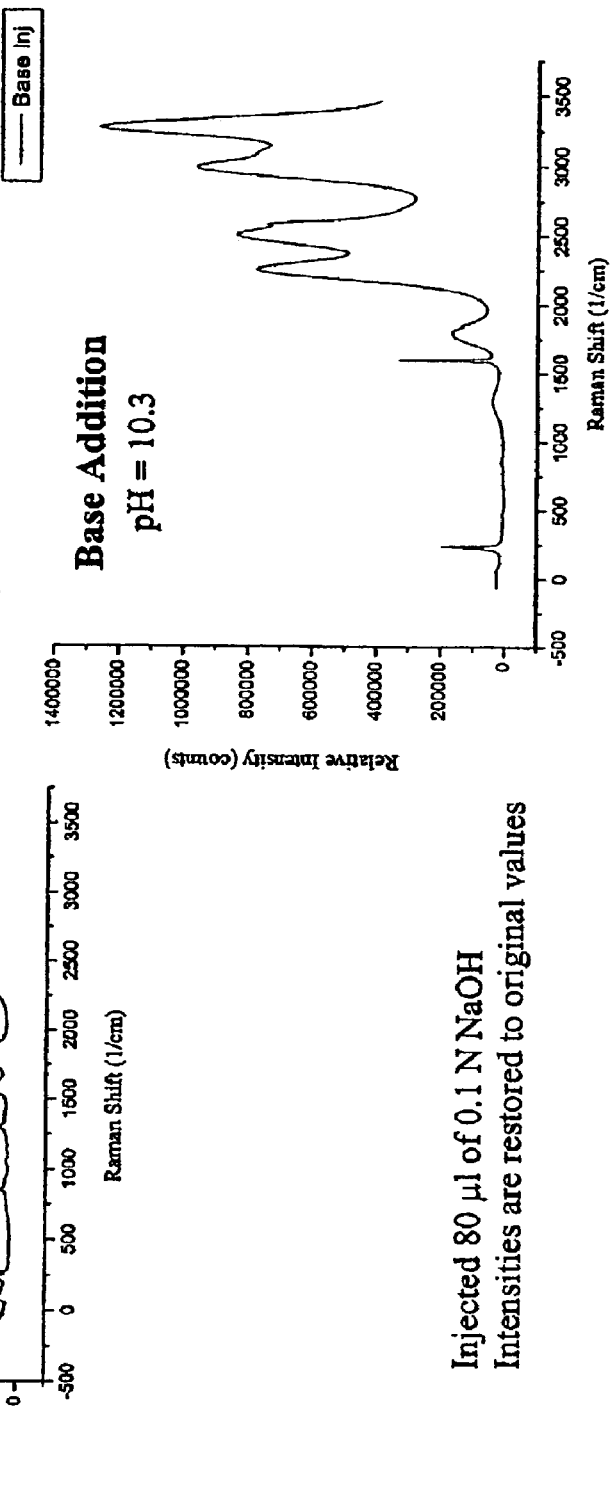
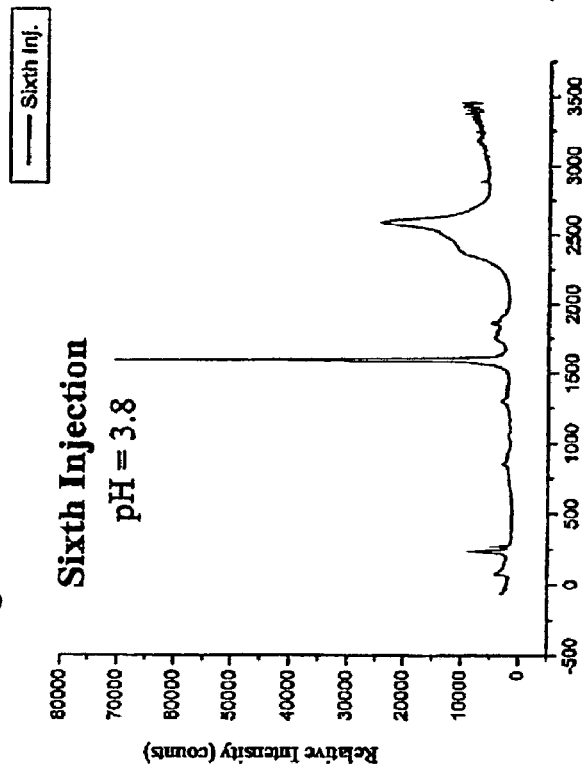
Figure 3G. Sixth Injection pH = 3.8. Injected 20 μl of 0.1 N HCl. No additional changes.
Figure 3H. Base Addition pH = 10.3. Injected 80 μl of 0.1 N NaOH. Intensities are restored to original values.

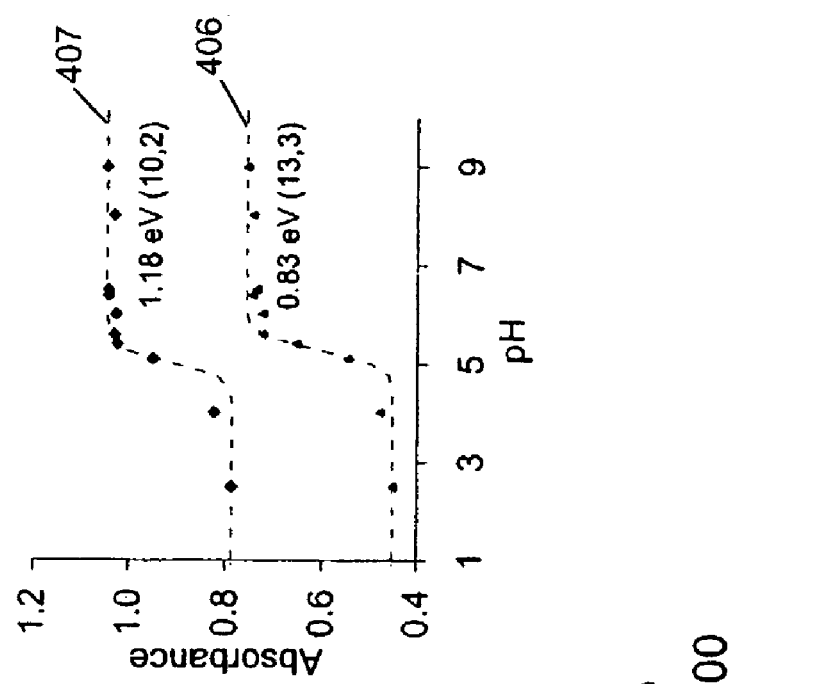
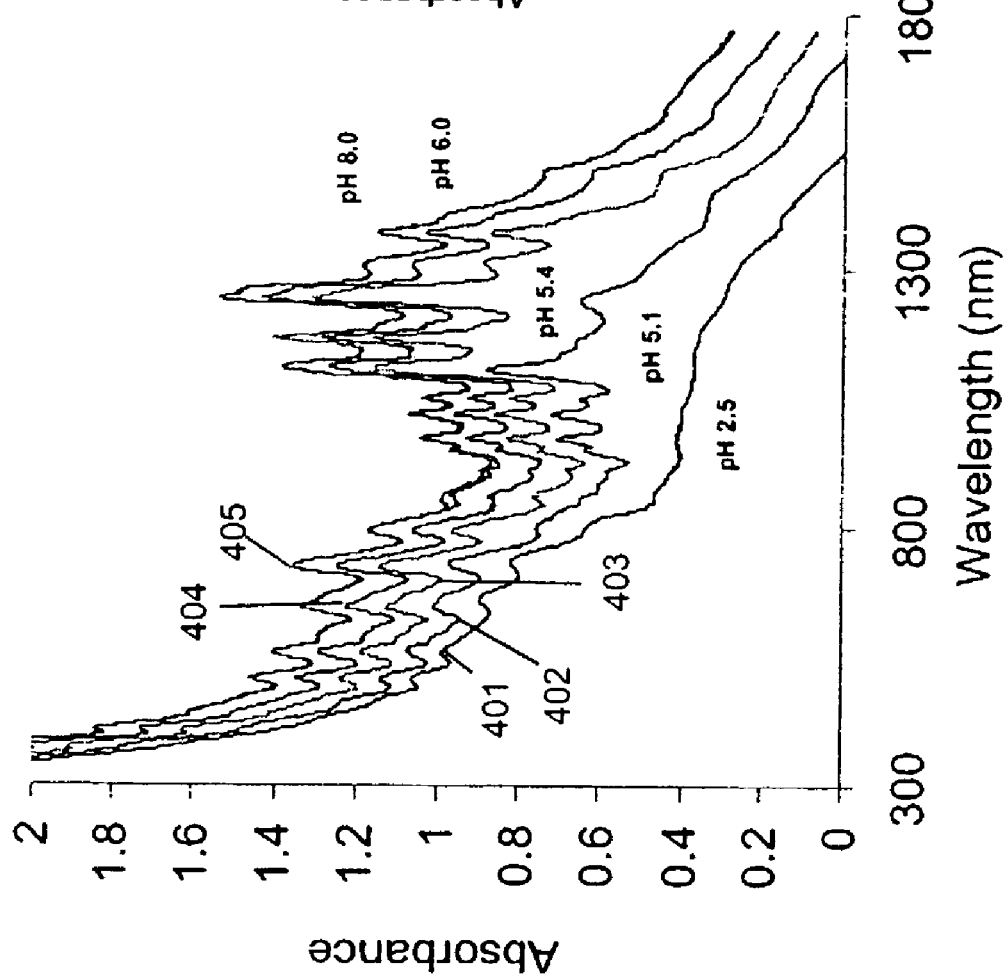
Figure 4A
Figure 4B

METHOD FOR SEPARATING SINGLE-WALL CARBON NANOTUBES AND COMPOSITIONS THEREOF

CROSS-REFERENCE TO RELATED APPLICATION

This application claims priority from U.S. provisional application Ser. Nos. 60/361,593 filed Mar. 4, 2002, 60/361,594 filed Mar. 4, 2002 and 60/390,887, filed Jun. 24, 2002, which applications are incorporated herein by reference.

This invention was made with United States Government support under Grant Nos. NSF DMR-0073046, NSF EEC-0118007 and NSF CHE-9900417 awarded by the National Science Foundation, Grant No. NASA-JSC NCC 9-77 awarded by the National Aeronautic and Space Administration and Grant No. N00014-01-1-0789 awarded by the Office of Naval Research. Funding was also provided by the Texas Advanced Technology Program Grant No. TATP 99-003604-0055-1999, and the Robert A. Welch Foundation Grant Nos. C-0689 and C-0807. The Government may have certain rights in the invention.

FIELD OF THE INVENTION

This invention relates generally to single-wall carbon nanotubes, and more particularly to a method for separating single-wall carbon nanotubes by type, to new materials and devices formed from these separated single-wall carbon nanotubes, and to methods for using these single-wall carbon nanotubes, such as for optical chemical sensors.

BACKGROUND OF THE INVENTION

Single-wall carbon nanotubes (SWNT), commonly known as "buckytubes," have unique properties, including high strength, stiffness, thermal and electrical conductivity. SWNT are hollow, tubular fullerene molecules consisting essentially of $sp^2$-hybridized carbon atoms typically arranged in hexagons and pentagons. Single-wall carbon nanotubes typically have diameters in the range of about 0.5 nanometers (nm) and about 3.5 nm, and lengths usually greater than about 50 nm. Background information on single-wall carbon nanotubes can be found in B. I. Yakobson and R. E. Smalley, *American Scientist*, Vol. 85, July–August, 1997, pp. 324–337 and Dresselhaus, et al., *Science of Fullerenes and Carbon Nanotubes*, 1996, San Diego: Academic Press, Ch. 19, ("Dresselhaus").

Several methods of synthesizing fullerenes have developed from the condensation of vaporized carbon at high temperature. Fullerenes, such as $C_{60}$ and $C_{70}$, may be prepared by carbon arc methods using vaporized carbon at high temperature. Carbon nanotubes have also been produced as one of the deposits on the cathode in carbon arc processes.

Single-wall carbon nanotubes have been made in a DC arc discharge apparatus by simultaneously evaporating carbon and a small percentage of Group VIIIb transition metal from the anode of the arc discharge apparatus. These techniques allow production of only a low yield of carbon nanotubes, and the population of carbon nanotubes exhibits significant variations in structure and size.

Another method of producing single-wall carbon nanotubes involves laser vaporization of a graphite substrate doped with transition metal atoms (such as nickel, cobalt, or a mixture thereof) to produce single-wall carbon nanotubes. The single-wall carbon nanotubes produced by this method tend to be formed in clusters, termed "ropes," of about 10 to about 1000 single-wall carbon nanotubes in parallel alignment, held by van der Waals forces in a closely packed triangular lattice. Nanotubes produced by this method vary in structure, although certain structures may predominate. Although the laser vaporization process produce can produce improved yields of single-wall carbon nanotubes, the product is still heterogeneous, and the nanotubes tend to be too tangled for many potential uses of these materials. In addition, the laser vaporization of carbon is a high energy process.

Another way to synthesize carbon nanotubes is by catalytic decomposition of a carbon-containing gas by nanometer-scale metal particles supported on a substrate. The carbon feedstock molecules dissociate on the metal particle surface and the resulting carbon atoms combine to form nanotubes. The method typically produces imperfect multi-walled carbon nanotubes, but under certain reaction conditions, can produce excellent single-wall carbon nanotubes. One example of this method involves the disproportionation of CO to form single-wall carbon nanotubes and $CO_2$ catalyzed by transition metal catalyst particles comprising Mo, Fe, Ni, Co, or mixtures thereof residing on a support, such as alumina. Although the method can use inexpensive feedstocks and moderate temperatures, the yield of single-wall carbon nanotubes can be low, with large amounts of other forms of carbon, such as amorphous carbon and multi-wall carbon nanotubes present in the product. The method often results in tangled carbon nanotubes and also requires the removal of the support material for many applications.

All-gas phase processes can be used to form single-wall carbon nanotubes. In one example of an all gas-phase process, single-wall carbon nanotubes are synthesized using benzene as the carbon-containing feedstock and ferrocene as the transition metal catalyst precursor. By controlling the partial pressures of benzene and ferrocene and by adding thiophene as a catalyst promoter, single-wall carbon nanotubes can be produced. However, this method suffers from simultaneous production of multi-wall carbon nanotubes, amorphous carbon, and other products of hydrocarbon pyrolysis under the high temperature conditions necessary to produce high quality single-wall carbon nanotubes.

Another method for producing single-wall carbon nanotubes involves an all-gas phase method using high pressure CO as the carbon feedstock and a gaseous transition metal catalyst precursor. ("Gas Phase Nucleation and Growth of Single-Wall Carbon Nanotubes from High Pressure Carbon Monoxide," International Pat. Publ. WO 00/26138, published May 11, 2000, incorporated by reference herein in its entirety). This method permits continuous nanotube production, and it has the potential for scale-up to produce commercial quantities of single-wall carbon nanotubes. This method is also effective in making single-wall carbon nanotubes without simultaneously making multi-wall nanotubes. Furthermore, the method produces single-wall carbon nanotubes in high purity, such that less than about 10 wt % of the carbon in the solid product is attributable to other carbon-containing species, which includes both graphitic and amorphous carbon.

All known processes for formation of single-wall nanotubes involve a transition-metal catalyst, residues of which are invariably present in the as-produced material. Likewise, these processes also entail production of varying amounts of carbon material that is not in the form of single-wall nanotubes. Hereinafter, this non-nanotube carbon material is referred to as "amorphous carbon."

All known methods of synthesizing single-carbon nanotubes also produce a distribution of reaction products, including, but not limited to, single-wall carbon nanotubes, amorphous carbon, metallic catalyst residues, and, in some cases, multi-wall carbon nanotubes. The distribution of reaction products will vary depending on the process and the operating conditions used in the process. In addition to the distribution of reaction products, the process type and operating conditions will also produce single-wall carbon nanotubes having a particular distribution of diameters and conformations.

The diameter and conformation of single-wall carbon nanotubes can be described using the system of nomenclature described by Dresselhaus. Single-wall tubular fullerenes are distinguished from each other by a double index (n, m), where n and m are integers that describe how to cut a single strip of hexagonal graphite such that its edges join seamlessly when the strip is wrapped onto the surface of a cylinder. When n=m, the resultant tube is said to be of the "armchair" or (n, n) type, since when the tube is cut perpendicularly to the tube axis, only the sides of the hexagons are exposed and their pattern around the periphery of the tube edge resembles the arm and seat of an armchair repeated n times. When m=0, the resultant tube is said to be of the "zig-zag" or (n, 0) type, since when the tube is cut perpendicular to the tube axis, the edge is a zig-zag pattern. Where n≠m and m≠0, the resulting tube has chirality and contains a helical twist to it, the extent of which is dependent upon the chiral angle. FIG. 1 diagrams the system of nomenclature for (n, m) nanotubes.

The electronic properties of single-wall carbon nanotubes are dependent on the conformation. For example, armchair tubes are metallic and have extremely high electrical conductivity. All single-wall carbon nanotubes can be categorized as metallic, semi-metals, or semiconducting depending on their conformation. For clarity and conciseness, both metallic tubes and semi-metal tubes will be referred to collectively as metallic nanotubes. For single-wall carbon nanotubes, about one-third of the tubes are metallic and about two-thirds are semiconducting. Metallic (n, m)-type nanotubes are those that satisfy the condition: 2n+m=3q, or n−m=3q where "q" is an integer. Metallic nanotubes are conducting with a zero band gap in energy states. Nanotubes not satisfying either condition are semiconducting and have an energy band gap. Generally, semiconducting nanotubes with smaller diameters have larger energy band gaps. Regardless of tube type, all single-wall nanotubes have extremely high thermal conductivity and tensile strength.

The particular nanotube diameter and conformation affects the physical and electronic properties of the single-wall carbon nanotube. For example, the strength, stiffness, density, crystallinity, thermal conductivity, electrical conductivity, absorption, magnetic properties, response to doping, utility as semiconductors, optical properties such as absorption and luminescence, utility as emitters and detectors, energy transfer, heat conduction, reaction to changes in pH, buffering capacity, sensitivity to a range of chemicals, contraction and expansion by electrical charge or chemical interaction, nanoporous filtration membranes and many more properties are affected by the diameter and conformation of the single-wall carbon nanotube.

The properties of a collection of a particular (n, m) selected carbon nanotube will differ from those of a mixture of single-wall carbon nanotubes that are made by the different production processes. The properties of mixtures of nanotube types represent a composite value over a distribution of property values. This composite value is generally not "average" behavior. In fact, the properties of composites can not only be inferior to, but also lacking altogether in a mixture of single-wall carbon nanotubes compared to those of a particular selected (n, m) type nanotube. Additionally, in the diameter range of single-wall carbon nanotubes, generally about 0.5 nm to about 3.5 nm, the alignment of the nanotubes to each other in closely-packed arrays, such as the well-known single-wall carbon nanotube "ropes", can be optimized when all the nanotubes are of the same diameter, minimizing misfits between tubes of different diameter.

While a method for separating and sorting single-wall carbon nanotubes of a specific type is desired in order to capture the desired properties of the selected nanotube type or types, such a method is complicated by two major factors. First is the nanotubes' extreme lack of solubility in water and most common solvents. Second is the strong propensity of single-wall carbon nanotubes to "rope" together in bundles that are strongly held together by van der Waals forces. The roping phenomenon aggregates different types of single-wall carbon nanotubes together in aligned bundles or "ropes" and holds them together with a sizable tube-to-tube binding energy of up to about 500 eV/micron. These aggregates generally contain random mixtures of metallic and semiconducting types of nanotubes with assorted diameters. When electrically contacted while in bundled aggregates, the carbon nanotubes experience sizable perturbations from their otherwise pristine electronic structure that complicates the differentiation between different types of nanotubes. Also, attempts to exploit the chemical diversity within mixtures of nanotubes, either through sidewall functionalization or end-group derivatization have not been successful in separating nanotubes of specific conformations, but have produced largely bundles of nanotubes or nanotubes with significantly altered electronic properties.

No effective process for making single-wall carbon nanotubes is known whereby significant quantities of carbon nanotubes made are of a single (n, m) type. Furthermore, to date, no methods for separating quantities of single-wall carbon nanotubes by (n, m) type are known, and no macroscopic quantity of such single (n, m) type single-wall carbon nanotube material has been produced. Macroscopic amounts of type-sorted single-wall carbon nanotubes that would provide the broadest range of possible nanotube properties and applications are heretofore unknown.

SUMMARY OF THE INVENTION

This invention relates to a method for sorting and separating carbon nanotubes, and in particular single-wall carbon nanotubes, by diameter and conformation, based upon the electronic and optical properties of the nanotubes. The invention also relates to compositions of selected nanotube types and sensing devices comprising them.

In one embodiment of the invention, single-wall carbon nanotubes are dispersed in a fluid, such that a certain fraction of the nanotubes have a net charge, and subjected to separation in an electric field. The single-wall carbon nanotubes migrate through the media under the influence of the electric field at a rate dependent on net charge, structure and chirality of the single-wall carbon nanotube. The nanotubes of different structure and chirality move at different rates, elute at different times, and are collected.

In another embodiment of the invention, single-wall carbon nanotubes are dispersed in a fluid, wherein the pH of the fluid is adjusted so as to cause a certain fraction of single-wall carbon nanotubes carry a net electric charge. The charge carried by each nanotube depends on its individual structure and chirality. The nanotube dispersion is then subjected to chromatographic separation in an electric field wherein the single-wall carbon nanotubes migrate through the fluid under the influence of the electric field at a rate dependent on their structure and chirality. The nanotubes of different structure and chirality elute at different times and are collected.

In yet another embodiment of the invention, single-wall carbon nanotubes are dispersed in an aqueous system wherein the nanotubes are surrounded by a generally non-perturbing coating, such as a micellular arrangement of surfactant molecules. A mixture comprising the nanotubes and the coating precursor, such as the surfactant, is vigorously agitated in order to coat individual nanotubes, which are subsequently separated from metallic catalyst residues and other carbon forms, such as nanotube ropes and amorphous carbon. The pH of the individually-dispersed nanotube suspension is made basic and then acidified to approximately neutral pH so as to protonate a first fraction of single-wall carbon nanotubes. The nanotube dispersion is then subjected to electrophoretic separation wherein the protonated single-wall carbon nanotubes migrate on a medium or diffuse through a fluid under the influence of an electric field at a rate dependent on the structure and chirality of the single-wall carbon nanotube. The nanotubes of different structure and chirality elute at different times and are collected. The steps of acidifying the remaining non-protonated portion of the nanotube mixture and electrophoretically the nanotubes are repeated step-wise until the entire population of nanotubes has been protonated and separated according to conformation and structure. Note the term "conformation" shall include all aspects of chirality or lack thereof. The term "structure" shall include all aspects of dimension, such as diameter and length.

Type-sorted single-wall carbon nanotubes can be used as individual (n, m) types, or in combinations of selected types, so as to obtain a mixture or composite material having the desired combination of nanotube properties. Type-selected nanotubes, and specific combinations thereof, provide the potential to achieve a continuous spectrum of material and electronic properties based on those possessed by individual types of single-wall carbon nanotubes. Density, strength, conductivity, optical properties, etc. can be adjusted incrementally by varying the amount of each (n, m) selected nanotube type to achieve the desired property or properties. The expanded range of material and electronic properties enables a wide variety of applications that heretofore have not been achieved with nanotube mixtures. Separated and type-selected single-wall carbon nanotubes provide specific properties useful in sensors, detectors, microelectromechanical devices, and numerous other applications.

Selected single-wall carbon nanotubes have spectral properties that are highly sensitive to their molecular environment. In particular, semiconducting nanotubes have been found to luminesce in the near-infrared portion of the electromagnetic spectrum. Chemical adsorbates on the nanotubes can affect, alter and modulate their spectral properties. The nanotubes are also sensitive to general conditions of the fluid environment, such as pH, temperature, pressure and flow. The nanotubes can sense these conditions as part of non-invasive optical probes, and are suitable for use in a nanoscale environment, including, but not limited to, living biological systems. The dynamic sensing capabilities of selected types of SWNT provide for a wide variety of sensing and monitoring applications.

BRIEF DESCRIPTION OF THE DRAWINGS

FIG. 3E shows a Raman spectrum of individually-suspended single-wall carbon nanotubes in a 1% $SDS/D_2O$ solution adjusted to pH 4.55.

FIG. 3F shows a Raman spectrum of individually-suspended single-wall carbon nanotubes in a 1% $SDS/D_2O$ solution adjusted to pH 4.07.

FIG. 3G shows a Raman spectrum of individually-suspended single-wall carbon nanotubes in a 1% $SDS/D_2O$ solution adjusted to pH 3.8.

FIG. 3H shows a Raman spectrum of individually-suspended single-wall carbon nanotubes in a 1% $SDS/D_2O$ solution adjusted to pH 10.3.

FIG. 4A shows a spectrophotometric titration of individually dispersed carbon nanotubes in SDS suspension as monitored by absorption. The absorption spectra are offset from pH 8 by a constant value to show changes.

FIG. 4B shows spectrophotometric changes in absorption for two particular semiconducting nanotubes as a function of pH.

DETAILED DESCRIPTION OF SPECIFIC EMBODIMENTS OF THE INVENTION

Figure 1:
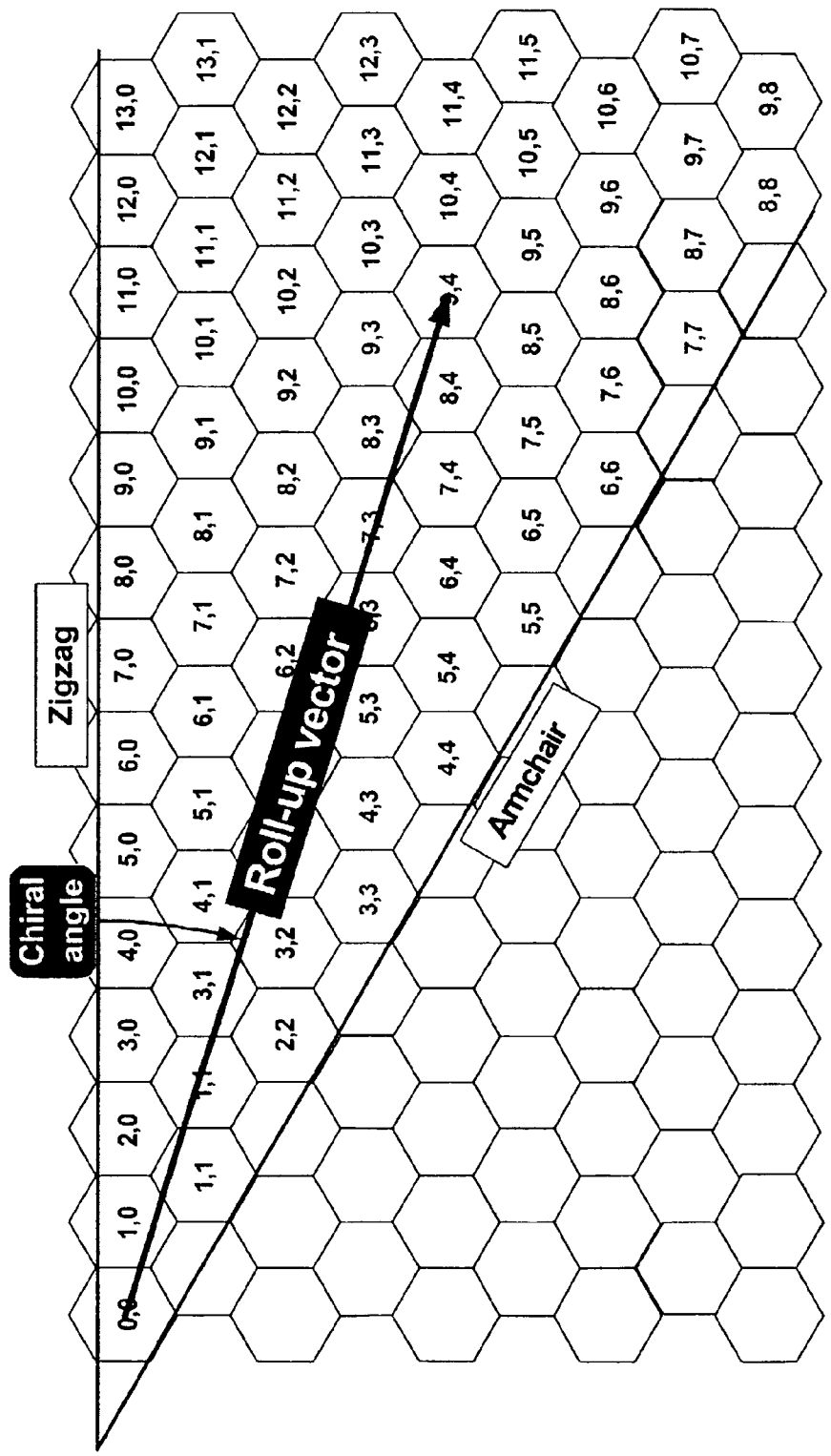
FIG. 1 diagram of the system of nomenclature for carbon nanotubes.

The invention relates to a process for sorting and separating carbon nanotubes by diameter and chirality type based upon their electronic and optical properties by dispersing the nanotubes, imparting a charge to a selective fraction of the nanotubes, and separating the nanotubes based on the nanotubes' net charge. The amount of charge that the nanotube can accommodate is a function of its electronic structure, diameter and conformation. The invention also relates to sensors comprising single-wall carbon nanotubes, wherein the metallic and semiconducting nanotubes can be separated from a mixture of nanotubes, and the sensing is accomplished by monitoring the sensitive electronic properties of the semiconducting nanotubes, which are capable of absorbing and luminescing in the near-infrared portion of the electromagnetic spectrum and provide a sensitive probe for a wide variety of applications. The electronic properties of the nanotube are very sensitive to the molecular environment and provide the capability of sensing adsorbates, chemical bonds, dipolar interactions and other fluid properties by perturbations in the luminescent spectra.

Separation of Different Types of Single-Wall Carbon Nanotubes

In one embodiment of the invention, single-wall carbon nanotubes are dispersed in a fluid, such that a certain fraction of the nanotubes have a net charge, and subjected to chromatographic separation in an electric field. The single-wall carbon nanotubes migrate through the media under the influence of the electric field at a rate dependent on net charge, structure and chirality of the single-wall carbon nanotube. The nanotubes of different structure and chirality migrate at different rates, elute at different times and are collected.

In another embodiment of the invention, single-wall carbon nanotubes are dispersed in a fluid, wherein the pH of the fluid is adjusted so as to cause a certain fraction of single-wall carbon nanotubes to protonate and carry a net electric charge. The nanotube dispersion is then subjected to an electrophoretic separation under the influence of an electric field wherein the single-wall carbon nanotubes migrate on a medium or through the fluid under the influence of an electric field at a rate dependent on their structure and chirality. The nanotubes of different structure and chirality migrate at different rates, elute at different times, and are collected.

In one embodiment, the single-wall carbon nanotubes are first dispersed in a fluid, such as an aqueous system containing a molecule, compound or polymer capable of wrapping, encapsulating or otherwise isolating the nanotubes from each other. With vigorous agitation and mixing, the nanotubes are dispersed in the aqueous system as individual carbon nanotubes and protected from reaggregation with a coating or wrapping that does not perturb the electronic properties of the nanotubes. In one embodiment, dispersal of the nanotubes can be accomplished by applying a non-perturbing coating to the nanotubes in a fluid, wherein the coating prevents reaggregation and/or bundling of the nanotubes. Shear mixing, sonication, and a combination thereof can be used to vigorously disperse the nanotubes as individual nanotubes. Since some fraction of the single-wall carbon nanotubes in the nanotube dispersion can be in the form of bundles or ropes, the dispersion can be centrifuged in order to separate the denser bundled, roped nanotubes and impurities from the individual nanotubes. After centrifugation, individual-dispersed nanotubes remain suspended in the supernatant portion of the fluid and can be decanted.

In yet another embodiment of the invention, single-wall carbon nanotubes are dispersed in an aqueous system wherein the nanotubes are surrounded by a generally non-perturbing coating, such as a micellular arrangement of surfactant molecules. A suspension comprising the nanotubes and the coating precursor is vigorously agitated in order to coat individual nanotubes, which are subsequently separated from metallic catalyst residues and other carbon forms, such as nanotube ropes and amorphous carbon. The pH of the individually-dispersed nanotube suspension is made basic and then acidified to approximately neutral pH so as to protonate a first fraction of single-wall carbon nanotubes. The nanotube dispersion is then subjected to an electric field wherein the protonated single-wall carbon nanotubes diffuse through the fluid under the influence of the electric field at a rate dependent on their structure and chirality. The nanotubes of different structure and chirality elute at different times and are collected. The steps of acidifying the remaining non-protonated portion of the nanotube mixture and separating in an electric field are repeated step-wise until the entire population of nanotubes has been protonated and separated by the electric field.

The fluid for dispersing the nanotubes can be water, polar solvents, hydrocarbon, oxygenated hydrocarbon, aminated hydrocarbon, aromatic, or any solvent that is compatible with the non-perturbing coating for the nanotube. Examples of solvents include, but are not limited to water, alcohols, acetic acid, dimethylformamide, and combinations thereof. Preferred solvents are polar solvents and water. Water is the most preferred solvent.

Non-perturbing coatings for the single-wall carbon nanotubes are coatings, molecules or polymers that do not interfere with or negligibly affect the electronic structure of the nanotube. For example, non-perturbing coatings that could be used include polymers, such as polyvinyl pyrrolidone (PVP), polystyrene sulfonate (PSS), poly(1-vinyl pyrrolidone-co-vinyl acetate) (PVP/VA), poly(1-vinyl pyrrolidone-co-acrylic acid), poly(1-vinyl pyrrolidone-co-dimethylaminoethyl methacrylate), polyvinyl sulfate, poly (sodium styrene sulfonic acid-co-maleic acid), polyethylene oxide (PEO), polypropylene oxide (PPO), dextran, dextran sulfate, bovine serum albumin (BSA), poly(methyl methacrylate-co-ethyl acrylate), polyvinyl alcohol, polyethylene glycol, polyallyl amine, copolymers thereof and combinations thereof. The polymers can wrap around the nanotubes and render the nanotubes soluble in water and other compatible solvents. Moreover, the polymer wrapping or coating can be removed without affecting the carbon nanotube structure. Further details of polymer wrapping of single-wall carbon nanotubes can be found in O'Connell, et al., "Reversible Water Solubilization of Single-Walled Carbon Nanotubes by Polymer Wrapping," Chem. Phys. Lett., Vol., pp. 265–271, 2001, and "Polymer-Wrapped Single-Wall Carbon Nanotubes," International Pat. Publ. WO 02/016257, filed Aug. 23, 2001, both of which are incorporated herein by reference.

Surfactants can also be used as non-perturbing coatings for suspending individual single-wall carbon nanotubes. "Surfactants" are generally molecules having polar and non-polar ends and which commonly position at interfaces to lower the surface tension between immiscible chemical species. Surfactants can form micellular assemblies with the nanotubes in an appropriate solvent medium. In an aqueous system, the non-polar tail of the surfactant molecules will surround the nanotube, with the surfactant molecules radiating outward from the nanotubes like spokes on a wheel in a micellular-like fashion with the polar end groups on the outside of the micelle in contact with the aqueous media. Anionic, cationic or nonionic surfactants, with anionic and nonionic surfactants being more preferred, can be used in an appropriate solvent medium. Water is an example of an appropriate solvent medium. Examples of anionic surfactants include, but are not limited to SARKOSYL® NL surfactants (SARKOSYL® is a registered trademark of Ciba-Geigy UK, Limited; other nomenclature for SARKOSYL NL surfactants include N-lauroylsarcosine sodium salt, N-dodecanoyl-N-methylglycine sodium salt and sodium N-dodecanoyl-N-methylglycinate), polystyrene sulfonate (PSS), sodium dodecyl sulfate (SDS), sodium dodecyl sulfonate (SDSA), sodium alkyl allyl sulfosuccinate (TREM) and combinations thereof. A preferred anionic surfactant that can be used is sodium dodecyl sulfate (SDS). Examples of cationic surfactants that can be used, include, but are not limited to, dodecyltrimethylammonium bromide (DTAB), cetyltrimethylammonium bromide (CTAB), cetyltrimethylammonium chloride (CTAC) and combinations thereof. An example of a preferred cationic surfactant that can be used is dodecyltrimethylammonium bromide. Examples of nonionic surfactants include, but are not limited to, SARKOSYL® L surfactants (also known as N-lauroylsarcosine or N-dodecanoyl-N-methylglycine), BRIJ® surfactants (BRIJ® is a registered trademark of ICI Americas, Inc.; examples of BRIJ surfactants are polyethylene glycol dodecyl ether, polyethylene glycol lauryl ether, polyethylene glycol hexadecyl ether, polyethylene glycol stearyl ether, and polyethylene glycol oleyl ether), PLURONIC® surfactants (PLURONIC® is a registered trademark of BASF Corporation; PLURONIC surfactants are block copolymers of polyethylene and polypropylene glycol), TRITON®-X surfactants (TRITON® is a registered trademark formerly owned by Rohm and Haas Co., and now owned by Union Carbide; examples of TRITON-X surfactants include, but are not limited to, alkylaryl polyethether alcohols, ethoxylated propoxylated $C_8$-$C_{10}$ alcohols, t-octylphenoxypolyethoxyethanol, polyethylene glycol tert-octylphenyl ether, and polyoxyethylene isooctylcyclohexyl ether), TWEEN® surfactants (TWEEN® is a registered trademark of ICI Americas, Inc; TWEEN surfactants include, but are not limited to, polyethylene glycol sorbitan monolaurate (also known as polyoxyethylenesorbitan monolaurate), polyoxyethylene monostearate, polyoxyethylenesorbitan tristearate, polyoxyethylenesorbitan monooleate, polyoxyethylenesorbitan trioleate, and polyoxyethylenesorbitan monopalmitate), polyvinylpyrrolidone (PVP) and combinations thereof. Preferred nonionic surfactants that can be used are alkylaryl polyethether alcohols, commercially known as TRITON-X® surfactants.

To facilitate the preparation and dispersion of the single-wall carbon nanotubes into individual tubes, the nanotubes and non-perturbing coating solution, e.g., the surfactant solution, are subjected to high-shear mixing. For clarity and conciseness, surfactant will be used as an exemplary example of a non-perturbing coating with the understanding that the same or similar conditions would apply for other non-perturbing coatings. To further facilitate dispersion, the nanotube-surfactant solution can be subjected to sonication or ultrasonication.

After forming a dispersion of the single-wall carbon nanotubes, the individually-dispersed nanotubes are separated from those nanotubes dispersed in bundles and from other non-nanotube solids. Centrifugation and ultracentrifugation are suitable means for separating the roped nanotubes and metallic impurities from the individually-dispersed nanotubes. With centrifugation, the dispersed nanotube bundles and metallic catalyst particles, usually with one or more layers of graphitic carbon overcoats, concentrate in the sediment at the bottom of the centrifuge tubes, while the individually-dispersed nanotubes remain suspended in the supernatant.

The supernatant contains a variety of individual single-wall carbon nanotube types surrounded by a protective non-perturbing coating. In the case of a surfactant, the coating can surround the nanotube in a micellular arrangement. In an aqueous media, when anionic surfactants form micelles, the non-polar tail components point in to the middle of the micelle, while the polar heads, with a negative charge, point out and are at the surface of the micelle. When the anionic surfactant surrounds an individual nanotube, the micellular arrangement is similar, except that a nanotube is in the middle of the micelle, surrounded by the non-polar tails of the surfactant. The outer portion of the nanotube-encased micelle, as in a conventional micelle in an aqueous system, comprises the polar heads of the surfactant.

The individually-dispersed nanotubes can then be separated according to nanotube type. To accomplish the separation, a charge is imparted to the nanotube. In one embodiment, the nanotubes are suspended in an aqueous environment wherein the nanotubes are surrounded by a surfactant molecules arranged in a micellular fashion. In an aqueous system, charge may be imparted to the nanotube by protonation. Protonation shall be defined as the close association of a proton ($H^+$) near or at the surface of the nanotube. Protonation can also encompass ions or other molecular species that can associate a proton near or at the surface of the nanotube. For example, a nanotube-encased micelle can be protonated by various compounds and ions, including, but not limited to, hydronium ion ($H_3O^+$), hydrochloric acid (HCl), hydrofluoric acid (HF), carbonic acid ($H_2CO_3$), sulfuric acid ($H_2SO_4$), nitric acid ($HNO_3$), fluorosulfuric acid ($FSO_3H$), chlorosulfonic acid ($ClSO_3H$), methane sulfonic acid ($CH_3SO_3H$), trifluoromethane sulfonic acid ($CF_3SO_3H$), oleum ($H_2SO_4/SO_3$) and combinations thereof.

Protonation alters the nanotube's chemical reactivity, electronic and optical properties and mobility in an electric field. Without being limited to theory, protonation can be performed selectively according to the band-gap energy of the nanotube and provides a means of selecting and separating nanotubes by type. The protonation process is readily reversible so that the carbon nanotubes can be restored to their pristine state once separation is completed. The separation and isolation of the nanotubes by type permits the concentration of individual single-wall carbon nanotubes of the same (n, m) type in order to produce macroscopic quantities that represent new compositions of matter. Macroscopic quantities are defined as a quantity of at least about 0.01 μg.

The selective protonation of the different nanotube types can be done by changing the pH of solution of suspended nanotubes and/or exposure of the nanotubes to certain gases, such as $CO_2$. Under acidic conditions, the selective protonation changes the charge on the nanotubes. Protonation also changes other properties of certain diameter nanotubes relative to others, hence creating a differential in properties that can be exploited in separation. Carbon nanotubes of certain types are protonated preferentially during the protonation process. For example, in a mixture of single-wall carbon nanotubes, the metallic nanotubes are protonated first, while the smallest diameter nanotubes, having the largest band-gap energy are the last to be protonated. Changing the charge on nanotubes as a function of their band-gap energy allows separation of the nanotubes by a variety of different means, including, but not limited to, chromatography, electrophoresis, and selective non-covalent functionalization, such as, for example, by macromolecular association or wrapping of the nanotube.

Selective protonation can be done by suspending the single-wall carbon nanotubes in a solution and decreasing the pH of a solution to a preset value. The particular pH value can determine the extent of protonation of the smaller band-gap, metallic nanotubes relative to the larger band gap, smaller diameter semiconducting nanotubes.

The separation of the nanotubes is based on each nanotube's electronic properties, which are dependent on and determined by the nanotube's structure and chirality. After individually dispersing the nanotubes, the pH of the nanotube dispersion is adjusted to basic conditions above pH 7. Adjustment of the pH to above basic conditions is conveniently done with a base, such as sodium hydroxide or Tris base buffer, also known as (Tris-hydroxymethyl) aminomethane. The first fraction of nanotubes is protonated by lowering the pH to about neutral with the addition of acid. The metallic nanotubes protonate under near-neutral conditions and, thus, are the first of the nanotubes to protonate. The semiconducting nanotubes are not affected. Separation of the first protonated fraction is accomplished by subjecting the complete mixture to an electrophoretic separation. In the presence of an electric field, the protonated nanotubes migrate in the field at different rates, relative to their structure. Under protonation conditions, the nanotube migration and separation can be monitored by spectroscopic means such as Raman, resonance Raman, absorption, luminescence and combinations thereof.

For selected nanotubes, near-IR detection can be used to monitor the separation of the nanotubes. Semiconducting nanotubes have been found to luminesce in the near-infrared. Since the luminescence is not observed under protonation conditions, monitoring the separation of the semiconducting nanotubes by near-IR fluorescence can be done by monitoring the fluorescence of the unprotonated semiconducting nanotubes. Under basic conditions and near-neutral pH, most semiconducting nanotubes will remain unprotonated and fluoresce in the near-IR. As the pH is lowered and certain semiconducting nanotubes protonate and will not fluoresce. The fluorescence will decrease with protonation and only be emitted from the non-protonated semiconducting nanotubes. A related method for monitoring the separation of the nanotubes with protonation is to monitor the absorption spectra of the nanotubes.

After sufficient migration time, the protonated nanotubes will separate into fractions of like-type nanotubes and can be collected for further use. Using tunable Raman spectroscopy or Raman at different wavelengths, each (n, m) type of nanotube from each nanotube fraction can be identified. Simultaneous and complimentary monitoring of the elution can be done by collecting absorption and fluorescence spectra of the eluted nanotubes. After separation and collection, the protonation can be reversed by the adjusting pH back to basic conditions.

After separation of the first fraction of single-wall carbon nanotubes, the pH of the unprotonated nanotubes is lowered by adding more acid in order to protonate a second fraction of nanotubes. As the pH is lowered, the semiconducting nanotubes will begin to protonate. In contrast to metallic tubes, semiconducting nanotubes are characterized by having a band gap in energy states. At about pH 5, the smaller band gap semiconducting nanotubes protonate. The resulting mixture is again subjected to an electric field wherein the protonated nanotubes migrate at a rate dependent on their structure. After sufficient migration time, the protonated nanotubes will separate into fractions of like-type nanotubes and can be collected for further use. When in the protonated state, the separation of the nanotubes into different fractions can be monitored by variable wavelength Raman and near-IR fluorescence and absorption spectroscopy. After collection of the different fractions of semiconducting nanotubes, the tubes may be typed by variable wavelength Raman spectroscopy.

Further separation of the mixture of nanotube types can be obtained by decreasing the pH even further. At lower pH, such as pH 3, the semiconducting nanotubes with the largest band gap, corresponding to the smallest diameter semiconducting nanotubes, will protonate. Again, the resulting nanotube mixture is subjected to an electric field and separated. As with the earlier fractionations, the protonated nanotubes migrate through the electric field at a rate dependent on their structure. After sufficient migration time, the protonated nanotubes will separate into fractions of like-type nanotubes and can be collected for further use. When in the protonated state, Raman and near-IR absorption and fluorescence spectroscopy can be used to monitor the separation of the nanotubes into different fractions. After collection of the different fractions of semiconducting nanotubes, the tubes may be typed using tunable Raman spectroscopy or Raman at different wavelengths.

In another embodiment, the separation of a mixture of nanotube types can be done in a step-wise fashion by decreasing the pH to protonate a certain nanotube fraction, applying an electric field to separate the protonated nanotubes, further decreasing the pH of the non-protonated fraction so as to protonate another fraction, and applying an electric field so as to separate a second fraction of protonated nanotubes. The steps of lowering of the pH to protonate a portion of the remaining non-protonated fraction and applying an electric field can be alternated until the entire mixture of nanotubes has been protonated and separated.

In another embodiment, the separation of the nanotubes can be done in a continuous fashion by continuously decreasing the pH while applying an electric field and collecting the separate nanotube fractions. The separation can be monitored by Raman spectroscopy using appropriate wavelengths. The separated nanotubes can be identified by Raman spectroscopy.

In one embodiment, the nanotubes that have been protonated are separated by differential migration in an electric field. Examples of this type of separation technique includes, but is not limited to, capillary electrophoresis, capillary electrochromatography, gel electrophoresis, paper electrophoresis, variations and combinations thereof. Capillary electrophoresis (CE) is also known as capillary zone electrophoresis (CZE). In capillary electrophoresis, the sample is added to a capillary filled with electrolyte and is exposed to an electric current. The charged nanotubes in solution move toward either the anode or the cathode and are also carried through the capillary by electroosmotic flow, the movement of the buffer ions toward one of the electrodes. Thus, the separation can be based on both nanotube charge and size. In capillary electrochromatography (CEC), the sample is loaded onto a capillary filled with a silica gel stationary phase such that in the presence of an electrical current, the separation is both electrophoretic and chromatographic. Capillary electrophoresis is a preferred embodiment for the separation of protonated nanotubes. Typically, the strength of the electric field is in the range of about 0.1 kV and about 30 kV.

In another embodiment, carbon nanotubes can be separated by type by adjusting the pH of a fluid containing a suspension of individually-suspended nanotubes by lowering the pH from about 7 to about 3 in the presence of oxygen to selectively protonate a population of nanotube types. Metallic nanotubes protonate near neutral conditions leaving semiconducting nanotubes unaffected. Small band gap semiconducting nanotubes protonate next as the pH is lowered to about 5. At about pH 3, all remaining semiconducting nanotubes are protonated.

After selective protonation, the nanotubes are separated to remove protonated or reacted nanotubes from unprotonated or unreacted nanotubes. Methods of separation include, but are not limited to, application of an electric field, selective binding, selective adsorption, chromatography, and combinations thereof. Capillary electrophoresis is a preferred method of separating the nanotubes. After separating the nanotubes, all fractions of nanotubes can be restored to their pristine state by increasing the pH to basic conditions, such as pH 10, with sodium hydroxide or other appropriate base.

In another embodiment, metallic nanotubes can be separated from a mixture of carbon nanotubes by methods using strong acids. Without being limited by theory, it appears that strong acids cause preferential ionization of metallic nanotubes, and enable their separation by means of electrophoretic, differential solvation or differential suspension methods. In nonaqueous media, strong acids can be used as the solution phase. Strong acids preferentially ionize metallic nanotubes and render them susceptible to electrophoretic type separations. Examples of strong acids that can be used to preferentially ionize metallic single-wall carbon nanotubes include, but are not limited to, such acids as trifluoromethane sulfonic acid ($CF_3SO_3H$), concentrated sulfuric acid ($H_2SO_4$), hydrochloric acid (HCl), hydrofluoric acid (HF), nitric acid ($HNO_3$), fluorosulfuric acid ($FSO_3H$), chlorosulfonic acid ($ClSO_3H$), methane sulfonic acid ($CH_3SO_3H$), and oleum ($H_2SO_4/SO_3$). Either as-synthesized or purified single-wall carbon nanotube material can be treated with strong acid and the metallic nanotubes separated using a variety of different techniques including selective solvation of the metallic nanotubes in strong acids, electrodeposition from strong acids, and electromigration in strong acid media to yield high concentrations of metallic nanotubes separated from the semiconducting types. The fractions can be precipitated out as separated fractions, washed to remove excess acid and filtered to remove solid matter.

Other embodiments of the process would include optimized parameters to decrease the time required for nanotube separation and the scaled process to accommodate large amounts of nanotube material. The initial starting pH of the sample affects both the time and efficiency of the separation. Thus, depending on the separation requirements for the desired application, the initial pH of the starting sample could be acidic, such as pH 5. The pH of the initial nanotube sample could also be in the basic range, such as pH 10.

The separation of the nanotubes can be done in a variety of ways in order to achieve the desired separation. Certain separation conditions may be used to facilitate separation of certain tube types. Other separation conditions may be employed to expedite the separation or increase the resolution between separate nanotube types or fractions. In one embodiment, the separation of the nanotubes can be done at different temperatures or the temperature can be ramped throughout the separation of the nanotubes. For example, the separation could be conducted at temperatures in the range of about 10° C. and about 40° C.

In other embodiments, the surfactant media used in the nanotube sample and the buffer solution can be the same or different. Buffer solutions of different types and pHs could be used for the separation of the nanotubes. The ionic strength of the nanotube sample and the buffer could be adjusted from that of the suspended mixture to the critical micellar concentration of the surfactant. Functionalization of the capillary wall can also be used to promote selective binding or interactions with certain nanotube species. The use of an applied pressure gradient from 0 to 10 psi across the capillary and a ramp in applied field are other possible embodiments. The field direction can also be reversed to negative (−) at the injection end and positive (+) at outlet.

Another variation in the separation step includes the type of separation means. For example, the nanotubes could be separated by gel electrophoresis, selective wrapping or binding followed by solvent transfer, chromatography or competitive adsorption of charged and uncharged nanotubes.

Macroscopic amounts of a particular (n, m)-type carbon nanotube represent a new composition of matter. Selected nanotube types have unique and discrete properties that are different than those of mixtures of nanotubes. The properties of matter comprised of such specific nanotubes can be selected and the amounts of the selected nanotubes adjusted to obtain combination of specific nanotube types that provide desired properties. An entire new class of matter is created by sorting the nanotubes by type, matter whose properties are, in effect, adjustable and tunable.

The invention provides a process for separating individual carbon nanotubes to yield new compositions of matter with new properties. The new matter consists of macroscopic amounts of type-sorted single-walled carbon nanotubes. Generally, macroscopic amounts of type-selected nanotubes could comprise at least about 15% of a selected (n, m) type of nanotube, i.e., a particular individual (n, m) nanotube type. Preferably, a macroscopic amount would comprise at least about 30% of a particular individual (n, m) nanotube type. More preferably, the macroscopic amount would comprise at least about 50% of a particular individual (n, m) nanotube type. More preferably, the macroscopic amount would comprise at least about 70% of a particular individual (n, m) nanotube type. More preferably, the macroscopic amount would comprise at least about 90% of a particular individual (n, m) nanotube type. The type-selected nanotubes would have a narrow range of electronic properties or the range of properties could be tuned by strategically combining certain amounts of selected types of nanotubes.

In another embodiment, the metallic type nanotubes are separated from the semiconducting nanotubes. The metallic nanotubes could, optionally, be further separated according to particular (n, m) types. With or without further separation by metallic type, macroscopic amounts of metallic nanotubes could be aligned and made into conducting fibers or nanotube wires, the conductivity of which could favorably compete with copper. A fiber or nanotube wire of a rope or bundle of nanotubes would be conducting if any of the nanotubes in the bundle were metallic and contacted metallic tubes along the longitudinal axis of the rope or wire. Concentrations of metallic nanotubes of at least about 15% for such an application would be preferred. The metallic nanotubes could be separated from the semiconducting nanotubes such that the resulting matter, in a macroscopic amount of single-wall carbon nanotubes, would comprise at least about 15% metallic-type nanotubes. Preferably, the macroscopic amount would comprise at least about 30% metallic-type nanotubes. More preferably, the macroscopic amount would comprise at least about 50% metallic-type nanotubes. More preferably, the macroscopic amount would comprise at least about 70% metallic-type single-wall carbon nanotubes. More preferably, the macroscopic amount would comprise at least about 90% metallic-type single-wall carbon nanotubes. Examples involving methods for making nanotube ropes can be found in "Method of Making Ropes of Single-Wall Carbon Nanotubes" U.S. Pat. No. 6,183,714, issued Feb. 6, 2001, which is included herein in its entirety.

With the ability to separate macroscopic quantities of any single-wall carbon nanotube type with high specificity, it is possible to use the type-selected tubes as seeds for growing even more of any selected nanotube type. Examples of a process for growing nanotubes from nanotube seeds can be found in "Process Utilizing Pre-formed Cluster Catalysts for Making Single-Wall Carbon Nanotubes," Int. Pat. Publ. WO 02/079082, published Oct. 10, 2002, and which is included herein in its entirety. This technique, in conjunction with those disclosed in the present application, enables bulk production of type-selected single-wall carbon nanotubes. Such production is useful in high volume applications such as composite materials where the properties of the material derive at least in part from the properties of the type-selected nanotubes. Examples include electrically- and thermally-conductive polymer composites. Materials with electrical or electromagnetic response(s) that are derived, at least in part, from the properties of the type-selected nanotubes. Another application enabled by this invention is the large-scale fabrication of electrical and electronic circuitry utilizing type-selected single wall carbon nanotubes. The availability of macroscopic amounts of type-specific nanotube material enables mass-production of nanometer-scale electronic circuitry. Specific type-selected single-wall carbon nanotubes can serve as an element of one or more electronic devices, including, but not limited to, interconnections between other devices, resistors, capacitors, diodes, transistors, pass elements, transducers, attenuators, heat transfer devices, memory elements, antennas, thermoelectric devices, piezoelectric devices, microwave circuitry, directional couplers, optoelectronic devices, electrochemical devices, fuel cell electrodes, fuel cell membranes, photoelectric cell electrodes, photoelectric cell active elements, circuit substrates, and heat conduction elements associated with electronic circuitry.

Optical Sensors Utilizing Luminescence of Selected Nanotube Types

Although Raman spectroscopy can be used to determine the particular diameter and conformation of all (n, m) nanotubes, definitive identification of the nanotubes can be done using variable wavelength Raman spectroscopy or Raman with different wavelengths of incident radiation, involves tedious and complicated analysis. It is now possible to expedite the analysis of various (n, m) nanotubes using the newly-discovered luminescence, and in particular, near-IR fluorescence of selected single-wall carbon nanotubes. The capability of using the near-IR region of the electromagnetic spectrum opens a wide variety of previously unknown applications, devices, and uses for nanotubes involving sensing and monitoring carbon nanotubes as a function of their chemical and physical environment. Near-IR fluorescence can be used, for instance, as a complimentary method to analyze and profile rapidly and to conveniently determine the composition of a mixture of nanotubes. Near-IR fluorescence can also be used in detectors or monitors using separated type-selected nanotubes. Alternatively, even without separation, near-IR fluorescence can be used to profile composition of nanotubes. The latter capability is particularly useful as a rapid method for "fingerprinting" as-produced nanotubes, and could be used as quality control technique.

The ability to separate certain (n, m) types or fractions of nanotubes, combined with the facile, versatile and robust capability of near-IR fluorescence detection provides an even broader variety of possible applications. Selecting semiconducting nanotubes and using near-IR fluorescence as a convenient, versatile and noninvasive means of detection enables the use of nanotubes as sensors for many applications, including in vitro applications in biological systems. Near-IR has the capability of being able to penetrate biological systems without altering or destroying tissue and, thus, could be used as a convenient non-invasive method to detect single-wall carbon nanotubes in biological systems.

In contrast to metallic nanotubes, which do not luminesce, semiconducting nanotube types are able to absorb radiation and luminesce in the near-IR. Note that luminescence can encompass fluorescence, phosphorescence, photoluminescence, other forms of optical emission, thermoluminescence, electroluminescence and combinations thereof. For semiconducting nanotubes, the diameter and chirality of the nanotube determine the electronic band-gap and hence the wavelength at which the nanotube will absorb incident photons and exhibit photoluminescence. Because nanotube luminescence is highly dependent on the electronic environment of the nanotube, the semiconducting nanotubes are very sensitive probes for monitoring and sensing changed electronic or chemical environment for a wide variety of different applications and uses. Additionally, the semiconducting nanotubes can be derivatized in such a manner, such as on one or both ends with one or more functional groups, such that the nanotube preserves its electronic signature. The functionalized nanotubes, due to the luminescent properties of the semiconducting structure, can be used as indicators in systems where the functional group may congregate, react or be preferentially absorbed.

ultraviolet portion of the electromagnetic spectrum (i.e., wavelengths in the range of about 300 nm and about 400 could be used for excitation of some small diameter semiconducting nanotubes.). Details of the structure assignment determinations and theory are given in Bachilo, et al., "Structure-Assigned Optical Spectra of Single-Walled Carbon Nanotubes," Science, Vol. 298, Dec. 20, 2002, p. 2361–2365, which is included herein by reference in its entirety. Table 1 give the emission and excitation frequencies for selected (n, m) semiconducting nanotubes and correlation with their predicted and observed Raman radial breathing mode frequencies ($v_{RBM}$).

TABLE 1

Spectral data and assignments for selected semiconducting SWNTs

| $\lambda_{11}$(nm) emission | $\lambda_{22}$(nm) excitation | $hv_{11}$(eV) emission | $hv_{22}$(eV) excitation | Assignment (n, m) type | Predicted $v_{RBM}(cm^{-1})$* | Observed $v_{RBM}(cm^{-1})$ |
|---|---|---|---|---|---|---|
| 833 | 483 | 1.488 | 2.567 | (5, 4) | 372.7 | 373† |
| 873 | 581 | 1.420 | 2.134 | (6, 4) | 335.2 | |
| 912 | 693 | 1.359 | 1.789 | (9, 1) | 307.4 | |
| 952 | 663 | 1.302 | 1.870 | (8, 3) | 298.1 | 297‡ |
| 975 | 567 | 1.272 | 2.187 | (6, 5) | 307.4 | |
| 1023 | 644 | 1.212 | 1.925 | (7, 5) | 281.9 | 283‡ |
| 1053 | 734 | 1.177 | 1.689 | (10, 2) | 265.1 | 264§ |
| 1101 | 720 | 1.126 | 1.722 | (9, 4) | 256.4 | |
| 1113 | 587 | 1.114 | 2.112 | (8, 4) | 278.3 | |
| 1122 | 647 | 1.105 | 1.916 | (7, 6) | 262.1 | 264§ |
| 1139 | 551 | 1.088 | 2.250 | (9, 2) | 289.7 | |
| 1171 | 797 | 1.059 | 1.556 | (12, 1) | 237.0 | 236♂ |
| 1172 | 716 | 1.058 | 1.732 | (8, 6) | 243.7 | |
| 1197 | 792 | 1.036 | 1.565 | (11, 3) | 232.8 | 233¶ |
| 1244 | 671 | 0.997 | 1.848 | (9, 5) | 241.4 | |
| 1250 | 633 | 0.992 | 1.959 | (10, 3) | 251.1 | 251‡ |
| 1250 | 786 | 0.992 | 1.577 | (10, 5) | 225.1 | 225¶ |
| 1263 | 611 | 0.982 | 2.029 | (11, 1) | 256.4 | |
| 1267 | 728 | 0.979 | 1.703 | (8, 7) | 228.9 | |
| 1307 | 859 | 0.949 | 1.443 | (13, 2) | 211.9 | |
| 1323 | 790 | 0.937 | 1.569 | (9, 7) | 214.9 | 215¶ |
| 1342 | 857 | 0.924 | 1.447 | (12, 4) | 207.5 | |
| 1372 | 714 | 0.904 | 1.736 | (11, 4) | 221.5 | |
| 1376 | 685 | 0.901 | 1.810 | (12, 2) | 227.0 | |
| 1380 | 756 | 0.898 | 1.640 | (10, 6) | 213.4 | |
| 1397 | 858 | 0.887 | 1.445 | (11, 6) | 200.8 | |
| 1414 | 809 | 0.877 | 1.533 | (9, 8) | 203.4 | |
| 1425 | 927 | 0.870 | 1.337 | (15, 1) | 193.6 | |
| 1474 | 868 | 0.841 | 1.428 | (10, 8) | 192.5 | |
| 1485 | 928 | 0.835 | 1.336 | (13, 5) | 187.2 | |
| 1496 | 795 | 0.829 | 1.559 | (12, 5) | 198.3 | |
| 1497 | 760 | 0.828 | 1.631 | (13, 3) | 203.4 | |
| 1555 | 892 | 0.797 | 1.390 | (10, 9) | 183.3 | |

*Using the expression $v_{RBM} = [223.5/d_t(nm)] + 12.5$ and assuming a C-C bond distance of 0.144 nm
†Raman excitation wavelength 830 nm.
‡Raman excitation wavelengths 633 nm and 636 to 672 nm.
§Raman excitation wavelength 1064 nm.
♂Raman excitation wavelength 782 nm.
¶Raman excitation wavelength 785 nm.

To optimize the use of type-selected nanotubes and provide for the rapid detection of the selected semiconducting nanotubes, the excitation and fluorescence emission frequencies have been correlated with Raman shifts using variable laser frequencies to determine the correspondence for each particular (n, m) tube type. Although the emission frequencies appear to be all in the near-IR portion of the electromagnetic spectrum (i.e., wavelengths in the range of 700 nm and 2000 nm), the excitation frequencies can range from the near-IR, through the visible (i.e., wavelengths in the range of 400 nm and 700 nm), and, even into the After establishing the identities of selected (n, m) nanotubes by correlations, such as given above, absorption and n-IR fluorescence can be used as spectroscopic means to monitor the separation of the nanotubes by selective protonation or other separation means. If near-IR fluorescence is used with selective protonation, the unprotonated semiconducting nanotubes will fluoresce. If the semiconducting nanotube has been protonated, the protonation of the nanotube can be reversed to higher pH conditions, such as by the addition of NaOH in order to observe fluorescence. Besides the ability to rapidly identify individual nanotube types, the near-IR fluorescence can be used to characterize a nanotube mixture without separating the individual fractions of nanotubes. In this embodiment, the nanotubes are dispersed in a liquid media with a polymer, surfactant or other molecule that can coat and isolate the nanotubes. The suspension is vigorously agitated, such as by shear mixing, sonication or combinations thereof, so that individual nanotubes are coated and suspended. The individually-suspended nanotubes are separated from ropes of nanotubes and other denser species by centrifugation, where the individually-suspended nanotubes remain in the supernatant. By scanning the supernatant recovered from centrifugation with appropriate excitation frequencies, the composition (i.e., identity and quantity) of the semiconducting nanotubes in a particular sample can be determined. This procedure could be used as a rapid method for characterizing nanotube samples as they are produced, such as a quality control tool.

The semiconducting nanotubes' ability to fluoresce in the near-IR optical frequency range provides a highly versatile and rapid detection method, enabling new, far-reaching areas of sensing and detecting, even as a non-destructive, or minimally invasive, sensor in biological systems. One of the advantages of being able to use excitation radiation and detect emission radiation in the near-IR is the ability to penetrate biological systems so that probes, sensors and detectors with nanotubes can be used in biological systems, including cells, tissues, interfacial membranes, and even living organisms.

In one embodiment, a plurality of single-wall carbon nanotubes is mixed with a polymer, surfactant or other moiety capable of isolating the nanotubes from interacting with each other. The mixture is vigorously agitated in order to coat or wrap the nanotubes with the isolating coating. The mixed system is centrifuged in order to aggregate bundles or ropes of nanotubes and other impurities in the sediment, while the individually-coated single-wall carbon nanotubes remain in the supernatant and can be decanted. Optionally, the nanotubes may be separated by (n, m) type or separated into fractions comprising groups of (n, m) nanotubes. Preferably, the semiconducting nanotubes are separated from the metallic nanotubes by protonating the metallic tubes, subjecting the mixture to an electrophoretic separation, wherein the metallic nanotubes migrate in the electric field and are separated from the semiconducting tubes. The semiconducting tubes, either as a group of mixed semiconducting tubes, or as further separated subsets of semiconducting tubes, or even as an individual (n, m) type semiconducting tube, can be used in various applications using near-IR fluorescence as a detector for semiconducting nanotubes.

The spectral properties of the nanotubes, and particularly the luminescence properties, are highly sensitive to their nanoscale environment. Chemical adsorbates on the nanotubes can alter these spectral properties and, consequently, the semiconducting nanotubes provide a sensitive optical sensing means for adsorbed gases, liquids and solids. The nanotubes are responsive to chemically, as well as physically, bound substituents, and can be used to sense general conditions of their environment, such as, but not limited to, pH, temperature, flow, pressure and changes in fluid dynamics and composition. They can also receive optical excitation and deliver electronic and thermal energy to their environment, such as by electrical and/or thermal luminescence.

The nanotubes are also self-monitoring, in that they are sensitive to their own condition and degree of association, and can sense conditions, such as, but not limited to, enclosure within a micelle in water suspension, encapsulation by a wrapped polymer, protein, or DNA, and intercalation by other materials such as acids. The nanotubes are spectrally sensitive to self-association with different tube types. For example, if metallic SWNTs are in proximity with semiconducting SWNTs, not only will the luminescence response of the semiconducting nanotubes be markedly reduced, but also the absorption and Raman spectra will also be altered. Even when separated by nanometers, nanotubes can sense this proximity with each other by dipole-dipole coupling, such that the luminescence characteristics of the nanotubes can be affected. Since each type of nanotube behaves uniquely in its environment, the use of a variety of different types of SWNTs can provide a matrix of data about the environment.

Due to their small nanometer size, type-selected semiconducting single-wall carbon nanotubes in a sensor device can sense conditions via non-invasive or minimally invasive optical probes. A light source in the UV, visible or near-IR provides for excitation of the nanotubes. Preferably, the light source is in the near-IR. The light source can be conducted by an optical fiber. The emitted or light returning from the nanotubes is detected by wavelength sensitive means and is subjected to spectral analysis. The spectral information obtained in turn provides information about the nanotubes and the chemical and physical environment.

In one embodiment, carbon nanotubes, that have been individually-dispersed and isolated so that they are not in contact with other nanotubes, and, optionally, type-selected, are suspended in a liquid inside a vessel such as, but not limited to, a capillary flow tube or mixing chamber in a microfluidics device. The vessel is fitted with a window or structure transparent to light, including that of the near infrared.

A light source, such as a conventional source, or a laser, such as a diode laser, is used to deliver light to the vessel containing the suspended nanotubes via optical fibers and/or conventional optics. As light strikes the nanotubes, the nanotubes absorb some of the light, and the semiconducting nanotubes become luminescent and emit fluorescent light. The transmitted light also contains spectral information about the nanotube environment.

The luminescent light is collected by optical fibers and/or conventional optics, and delivered to a spectrometer for spectral analysis. The various emitted wavelengths are detected and a spectrum is recorded in a computer. Similar apparatus setups can also be used to obtain spectral information from Raman scattering and from absorption spectral analysis.

One embodiment of a suitable apparatus for detecting and sensing adsorbed and dissolved gases, such as carbon dioxide, isolated single-wall carbon nanotubes dispersed in an aqueous media. A diode laser emitting red light in the range of 780 to 790 nm is transmitted by an optical fiber and focused into a vessel outfitted with an optically transparent means. Many silica-based glasses are suitable for this purpose. The vessel contains encapsulated carbon nanotubes, such as in sodium dodecyl sulfate (SDS) micelles, prepared that at least some, are individually (i.e., not as ropes or bundles) suspended in water. The resultant fluorescence and Raman scattered light is collected by an optical lens and transmitted through one or more optical fibers to a spectrometer. The scattered laser light is rejected by a filter means. The emitted light is dispersed and detected by an array detector, such as an Indium-Gallium-Arsenide (In-GaAs) detector, or a charged-coupled device (CCD) camera. The electronic signal is recorded by a computer so as to correlate the intensity of the emitted light as a function of wavelength or frequency shift in the case of Raman scattering.

The emitted light comprises a spectrum of fluorescent features, or peaks, extending from about 870 nm to about 1400 nm. Various diameter nanotubes emit various wavelengths, with the larger diameter nanotubes generally emitting longer wavelengths. When molecules adsorb onto the walls of the nanotube, these spectra features are altered. The longer wavelength features are generally altered first, as the concentration of the adsorbate molecules increases.

As with many molecular species, when carbon dioxide, used here as an example of an absorbed gas, is present in the water, the fluorescence spectra being acquired will be altered. For lower concentrations, the longer wavelength emission derived from the larger nanotubes diminishes first, and is monotonically decreasing with increasing concentration. As the concentration increases, the longer wavelength fluorescence is extinguished. The shorter wavelength fluorescence from the smaller nanotubes then diminishes with increasingly high concentration. The signal intensities are compared to a reference spectrum for nanotube without the adsorbed gas. The concentration of the carbon dioxide adsorbate, or other gases or liquids, can then be determined. Since the spectral properties change as a water suspension of SWNTs is exposed to varying levels of dissolved carbon dioxide, the nanotubes provide the basis for a quantitative sensor.

Like devices and procedures can be used to measure the compositions of nanotube samples and the surrounding environmental conditions, such as, but not limited to factors of acidity, concentrations of dissolved gases, liquids, and solids, temperature, etc.

The SWNT sensor can be used as a chemical "nose" to monitor adsorbates such as ozone, carbon dioxide, ammonia, halogens, nitrogen oxides, oxygen, and other rather reactive species that can also be environmental pollutants in air and water. The SWNT sensors can also be used in micro-reactor, microfluidic, microelectronic applications, as cellular based chemical sensors, sensors in lipid bilayers, sensors at catalyst surfaces, sensors attached or interacting with enzymes. Furthermore, the SWNT sensors can be used to monitor dissolved liquids, especially those prone to electron donor-acceptor bonding or hydrogen bonding, such as ketones, alcohols, ethers, carboxylic acids, esters, amides, hydroxyl-containing molecules, and substituted aromatic compounds. They can also be used to monitor dissolved or suspended solid materials such as polymers and to monitor the binding of metallic species which may also act as quenchers.

Some embodiments of the present invention are directed toward chemical applications where SWNT sensors provide an optical titration monitor as acid, base, or any other reactant is added and consumed. In other embodiments, the SWNT sensors provide an in-situ monitor to track-reaction progress. In some embodiments of the present invention, a known variety of SWNT sizes can be used as a multi-wavelength sensor for pH, flow, temperature, oxidation potential, and alterations due to exposure to light. In some embodiments, molecules that are not adsorbed on the nanotube can be detected by overtone quenching of the energy transfer between separated nanotubes. In yet another embodiment, the degree of alignment in a polymer by polarization of scattered light could be monitored using selected nanotubes as probes or polymer intercalants.

Methods of using SWNT sensors/probes can include biomedical applications. Such applications benefit from the fact that living tissue and cellular matter are essentially transparent to light with frequency in the near infrared (NIR). These methods are largely microscale applications of the chemical applications described above. These methods include measuring the change in fluorescence intensity and/or lifetime due to chromophores on adjacent proteins, nucleic acids other chromophores. Spectrally absorbing species, especially with large chromophores, such as those containing porphyrins will be detectable by the altered the fluorescence. Other biomedical applications involve cytometry type sorting based on the fluorescence signal. SWNTs in a droplet with adherent proteins, cells, etc. show a changed lifetime or intensity and may be selected and separated. In still other embodiments of the present invention, carbon nanotubes can be attached to a monoclonal antibody and luminescence spectroscopy can be used to monitor the degree of nanotube localization. A pulsed IR laser can then be used for selective thermal denaturation and localized damage to malignancies.

In embodiments of the present invention, carbon nanotubes can be used to measure surfactant concentration. Carbon nanotube monitors can yield very accurate information concerning drug delivery, transport and micelle interactions based upon the SDS response in these cases. In embodiments wherein the SWNT sensors are mounted on a porous membrane to create a flow-through device, the concentration of surfactant, counter-ions, and electrolyte in general can be detected continuously in real-time. This permits the monitoring of fluid mixing, flow, shear effects, laminar behavior, and gas flux across a membrane.

Methods of using the SWNT sensors can further include monitoring SWNT conditions. Such sensors can be used to determine nanotube type, diameter, chirality, length, as well as the distribution of such characteristics in an aggregation, bundle, rope, fiber or film. The SWNT sensors can be used to determine the presence of adsorbates, contamination, chemically bound species, oxidation, metal catalyst, other fullerenic species, other carbon contamination, purity, long range order and disorder, and excited electron scattering species. The SWNT sensors can be used to determine the presence and amount of intercalating species in ropes, films, and bundles of nanotubes. They can be used to determine the degree of alignment of nanotube fibers and films by polarized Raman and Rayleigh scattering. They can be used to determine degree of self-association, and the presence of metallic nanotubes aggregated with semiconducting nanotubes. They can be used to monitor the degree to which SWNTs are "wrapped" with polymer or incorporated into an anionic micelle such as SDS, a cationic micelle such as dodecyl trimethyl ammonium bromide, or a neutral micelle such as Triton-X. They can also be used to monitor the presence of any electron-donor acceptor (EDA) or hydrogen-bonded reversibly-adsorbed species.

Carbon nanotube sensors can be used to measure, monitor and optimize a number of SWNT processing conditions. These include finding optimal sonication times, temperature and environment, monitoring separation processes such as adsorption on a substrate, high-performance liquid chromatography (HPLC) separations, membrane-based separations, solvent extraction, phase inversion, and magnetic separations.

Additionally, other, more varied methods of using SWNT sensors include monitoring the efficacy of electrophoresis, electrostatic separation, chromatography, HPLC (High Performance Liquid Chromatography), supercritical fluid chromatography, gas chromatography, and magnetic chromatography; and using nanotubes individually or in thin films or fibers as electroluminescent sources for sensing, communications, or computing, and as photoconductive solids for optically active circuit elements for sensing applications.

Wavelength-selected light can be used to protect the nanotubes with the corresponding absorption from protonation so that it can be selectively wrapped with PVP or another material. This selected-diameter nanotube is then physically separated from the mixture of other nanotubes. Selective absorption of laser light, especially pulsed laser light, can disrupt micelles and polymer wrapping which can in turn lead to selective flocking. In other embodiments of the present invention, selected diameters and types of SWNTs are placed in a transparent matrix (such as polymers like PVP or glasses), or in a thin film, which can be used as fluorescent and absorption filters, especially in the near infrared, with the selection of nanotube types that determine the wavelength(s) that are transmitted. Such a filter made with a single type of SWNT with the corresponding absorption band can be used as a laser line blocker.

The SWNT sensors can also be dispersed individually in a liquid. They can also be made to "float" in a gaseous environment. In other embodiments, the SWNT sensors are "anchored" to a substrate in either a random or oriented manner. If oriented, they can be parallel to the substrate, perpendicular to the substrate, or combinations of the two. These can rely on only one nanotube or rely on a plurality of nanotubes.

The small size, chemical inertness, and physical robustness of the carbon nanotubes makes these useful as in situ probes for micro- and nanoscale fluid containing devices, as well as for a living cell. When a transparent means is integral to the vessel being probed, such as a cell wall, then no additional transparent means need be added. In such circumstances, a single carbon nanotube may be sufficient as the sensor. The optical fiber may then be directly coupled to the vessel without an intervening lens. A single mode optical fiber provides the most effective delivery and return of light from a small volume, and in this case the same optical fiber can serve both functions. As an example of a microscale application, the "breathing" of a single cell might be monitored.

In embodiments of the present invention, the SWNT(s) may be anchored onto an end of an optical fiber, rather than being in suspension in the liquid being probed. In this form, it constitutes an "optrode," or optical sensing probe. A viable cell whose metabolism is altered by biological materials in the surrounding solution will change its generation of carbon dioxide and this can be sensed by the optrode. In this application, there may be clusters or aggregates of like SWNTs for increased sensitivity. It is preferable that aggregates of dissimilar nanotubes be kept separate to minimize energy transfer. Such aggregates should preferably be somewhat porous so as to allow intercalation and circulation of the fluid being probed. An alternative embodiment utilizes dissimilar, but non-quenching nanotubes to "funnel" excitation to one type of SWNT which will draw on the excitation energy of the surrounding nanotubes and will exhibit considerably enhanced signal, concentrated in a single wavelength peak, compared to its own excitation. This will allow the substitution of a single detector in place of the camera and disperser.

The optical device may also function on the principle of absorption, rather than emission. In these embodiments, the light source is broadband or "white light," rather than a laser. In some, the light passing through the optical fiber can undergo attenuated total internal reflection (ATR) in a prismatic means at the probe end of the optical fiber. Carbon nanotubes attached to or near the reflecting surfaces of the prism optrode absorb some of the wavelengths, which varies according to the type and concentration of adsorbates. The altered spectral signal returns up the optical fiber, and into a spectrometer means, and the signal is processed in a computer. The type and concentration of dissolved matter in the fluid is then determined. The ATR surface may comprise part of the fluid enclosure of the vessel, or may have a biological cell(s) attached to it, or it may be placed in contact with tissue that have nanotubes incorporated.

In certain embodiments, the probe may be an optical fiber with the light propagating in the core and the cladding thinned or removed to allow an evanescent wave to propagate into the medium to be probed. The signal light passes back into the source optical fiber, or an adjacent optical fiber. The optical fiber has nanotubes either attached to its surface, or in the surrounding medium to be monitored. The light conducting means may also be hollow or tubular, with a fluid flowing through and at least partially surrounded by the evanescent wave of the excitation light.

In further embodiments, the nanotubes may also provide a light source in the near infrared. Thin film assemblies of like nanotubes can be made to provide narrowband infrared luminescence with an electric current. The luminescence wavelength will correspond to that seen for optically excited fluorescence. Mixtures of nanotube types can alter the spectral emission. These devices can provide useful light sources for sensing, optical communication, and computing applications. They comprise a tunable or wavelength adjustable infrared laser source. Excitation of such light sources can be by laser, lamp, LED illumination, or electro-luminescence or direct electrical excitation from an alternating, inductively coupled, or direct current passing through the SWNT. Use of shorter wavelength lasers, such as the frequency-doubled Nd:YAG laser at 532 nm, and the argon ion at 514 or 488 nm enhances the sensitivity to metallic SWNTs. Pulsed illumination or high frequency modulation will be utilized for lifetime measurements.

In other embodiments, monitoring the Raman frequency shift, as well as the intensity changes, can be used to sense the surrounding chemical environment. This appears to be especially suitable for use as a monitor of oxidation and reduction, with the frequency shift increasing for oxidation (electron charge withdrawal) of the nanotube. The G' two-phonon peak decreases with the degree of sidewall association.

In methods of using the SWNT sensor devices of the current invention, there are many additional locations for the carbon nanotube sensors, such as: (a) fixed, anchored on substrate; (b) fixed on the end of an optical fiber "optrode;" (c) fixed to electrical conductor and current source for electro-luminescence; (d) SWNTs bound to an electrode surface; (e) floating in gas stream, injected by electrospray, or by laser ablative suspension, where they are then airborne and can probe the gas stream for adsorbates; (f) embedded in porous polymer matrix as support for liquid or gas (i.e., gases flowing through then alter the fluorescence as they adhere to the nanotubes and this will make the polymer more conductive if metallic tubes are used); (g) nanotubes on aerogels and low density supports for high surface area gas sensors, and (h) embedded in an inorganic (e.g., ceramic) matrix for high temperature sensors.

In other embodiments, light and heat may be used to clean and restore the sensing capability on the nanotubes. For many of these cases, ultraviolet and/or light flash desorption can remove adsorbates. Carbon nanotubes and light can be used to generate gases, such as hydrogen, and promote boiling.

Besides single-wall carbon nanotubes, nanotube separation and sensors based on near-IR absorption and fluorescence should be considered to be applicable to multiwall carbon nanotubes, as well as other nanotubes with extensive pi cloud conjugation, such as those made of boron nitride. Double-wall carbon nanotubes are an example of a multi-wall carbon nanotube. In this case, there is a statistical probability of 1/9 th that both nanotube shells will be metallic, 4/9 ths that both shells will be semiconducting, and 4/9 ths that one shell will be semiconducting and one shell metallic. Nanotubes with at least one metallic tube (5/9 ths of total) are expected to behave like metallic nanotubes and not exhibit fluorescence, leaving 4/9 ths of the total having the possibility of exhibiting near-IR fluorescent behavior. The economics and availability of double-wall nanotubes and other multi-wall nanotubes could provide cost-effective sensors for certain sensor applications.

Because these devices and apparatus are based on newly discovered near-infrared photoluminescence of carbon nanotubes, they are the first devices to exploit that photoluminescence. This luminescence was previously unknown, and it is expected that therefore substantially all such applications utilizing photoluminescence described here will be novel. The invention utilizes single walled carbon nanotubes that by appropriate preparation, also provide unusually distinctly sharp absorption and resonance Raman spectroscopic features; it is expected that therefore many such applications described here will also be novel. These nanotubes are physically, chemically, and optically very robust. They will allow for the development of a wide variety of in situ and non-invasive sensors and chemical "noses", suitable for use in microfluidics and biomedical applications.

The carbon nanotubes have been appropriately separated and prepared, and are suspended in a liquid inside a vessel such as a capillary flow tube or mixing chamber in a microfluidics device. The vessel is fitted with a window or structure transparent to light, including the near infrared.

One embodiment of the invention is a device comprised of a narrowband or broadband light source, an optical means of delivering the light, a vessel which may be fitted with an optically transparent window or region with one or more SWNTs anchored or freely suspended in the medium to be monitored and capable of receiving the light, a optical means to collect the light and transmit it to a spectrometer, a wavelength selective instrument capable of selecting one or more wavelengths of light utilizing dispersion, interferometric, or other means, a light sensitive detector, array detector, or a CCD detector capable of detecting light in the near infrared region of the spectrum and converting it to an electrical signal, and a computer for recording and analyzing the signal.

Devices that rely on disaggregated single-walled carbon nanotubes can require special preparation. The micelle suspensions, or nanotubes wrapped with PVP or other polymers may tend to come out of suspension under some circumstances. For free-floating sensor applications, it may be necessary to filter out the nanotubes in a subsequent step.

Many other changes in the chemical conditions can also be sensed with the use of a luminescent probe. Some examples include, but are not limited to, monitoring other dissolved gases, determining the presence of other liquids, such as alcohols and ketones dissolved in the water, and sensing dissolved solids. Changes in photoconductivity of the nanotubes can also be considered as adsorbates come in near contact with the nanotubes by comparing changes peak ratios in the near-IR fluorescence and visible with varying adsorption.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This example demonstrates the preparation of a dispersion of individual single-wall carbon nanotubes in a fluid media and the detection of fluorescence from semiconducting-type single-wall carbon nanotubes. Raw HIPCO® single-wall carbon nanotube product (HIPCO is a registered trademark owned by Carbon Nanotechnologies, Inc., Houston, Tex.), from a high-temperature, high-pressure CO disproportionation process was dispersed in 200 mls of aqueous 1 wt % sodium dodecyl sulfate (SDS) surfactant solution by high-shear mixing (Polyscience X-520) for one hour. The resulting dispersion was treated in a cup-horn sonicator (Cole Palmer CPX600) for 10 minutes at a power level of 540 W. Immediately following sonication, samples were centrifuged (Sovall 100S Discovery Ultracentrifuge with Surespin 630 swing bucket rotor) at 122,000 g for 4 hours. The upper 75% to 80% of supernatant was then carefully decanted, giving micelle-suspended nanotube solutions at a typical mass concentration of 20 to 25 mg/liter. For some experiments, these nanotube samples were further processed for competitive wrapping with a polymer by adding about 1 wt % of 40 kDa poly(vinylpyrrolidone) (PVP) to the SDS suspension. Analysis of samples by atomic force microscopy showed most nanotubes to be about 80 to about 200 nm long, with an average length of 130 nm. This length distribution is typical of heavily sonicated fullerene nanotubes from a wide range of sources and is believed to arise from sonication-induced tube cutting. However, spectra of these samples, including Raman features, such as strong radial breathing modes (RBM) and the near absence of the "disorder peak" near 1330 $cm^{-1}$, strongly suggest that this sonication has not substantially damaged the tube side walls. TEM, X-ray diffraction, and RBM Raman measurements indicate tube diameters between 0.7 and 1.1 nm, typical of HiPco single-wall carbon nanotube diameters.

Figure 2:
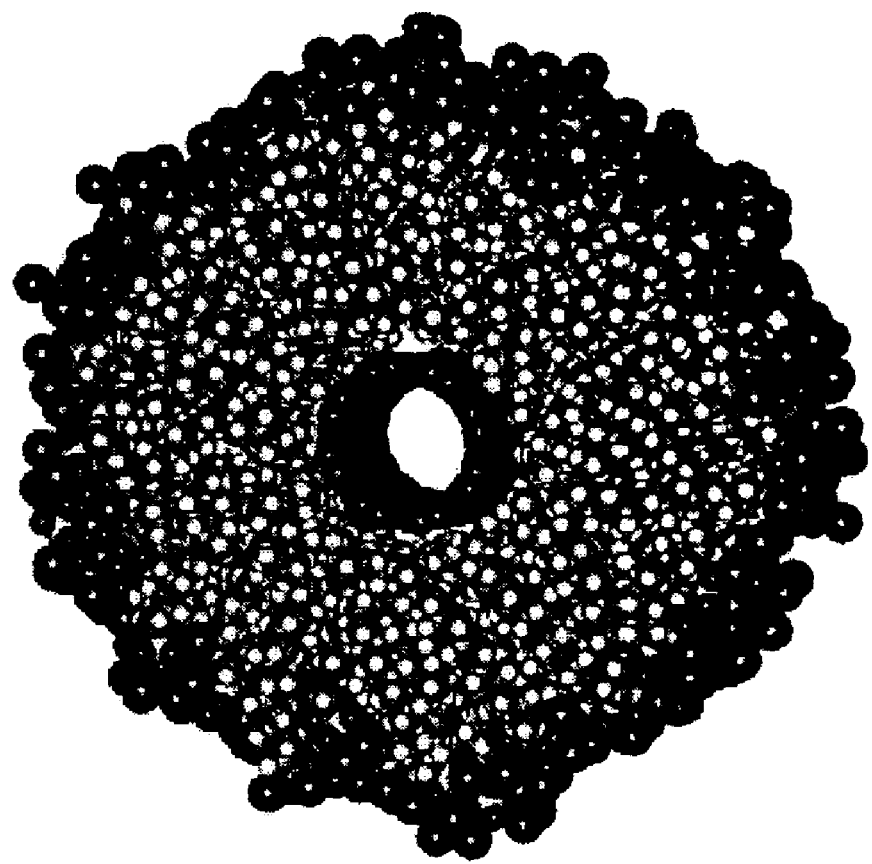
FIG. 2 shows a single-wall carbon nanotube surrounded by surfactant molecules arranged in micellular fashion around the nanotube.

FIG. 2 shows an individual single-wall carbon nanotube encased in one possible configuration of a closed-packed columnar sodium dodecylsulfate (SDS) micelle, which has a specific gravity of approximately 1.0, whereas the specific gravity of an SDS-coated 7-nanotube bundle would be approximately 1.2. In centrifugation, nanotube bundles of nanotubes and 3 to 5 nm diameter residual iron catalyst particles, each overcoated with one or two atomic layers of carbon, with a density of about 2 to 3 $g/cm^3$, congregate at the bottom of the centrifuge tube, leaving a supernatant highly enriched in individual nanotubes, even in $D_2O$ (density 1.1 $g/cm^3$).

The SDS suspension of individual nanotubes was found to be much more stable than suspensions of nanotube bundles produced by milder sonication. Samples containing 20 mg/liter of nanotubes in 1 wt % SDS survived heating to 70° C., addition of up to 40% methanol, NaCl concentrations up to 200 mM, and $MgCl_2$ concentrations up to 10 mM for periods of greater than 24 hours without flocculation.

EXAMPLE 2

Figure 3B:
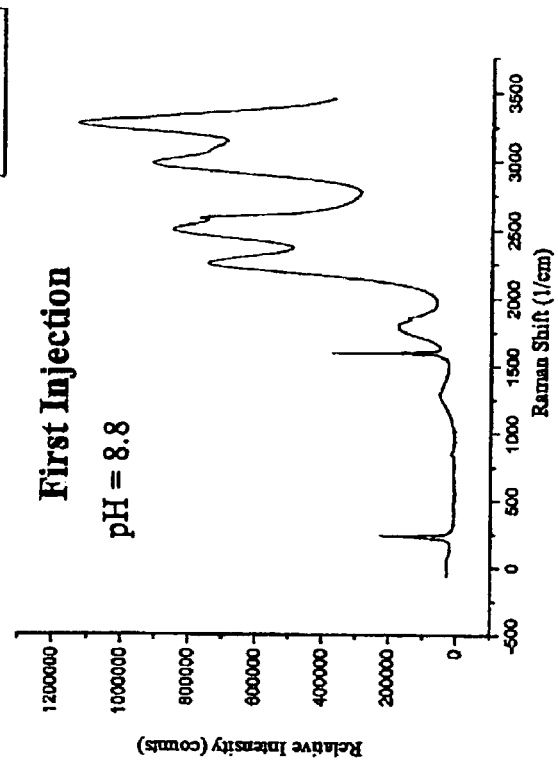
FIG. 3B shows a Raman spectrum of individually-suspended single-wall carbon nanotubes in a 1% $SDS/D_2O$ solution adjusted to pH 8.8.
Figure 3A:
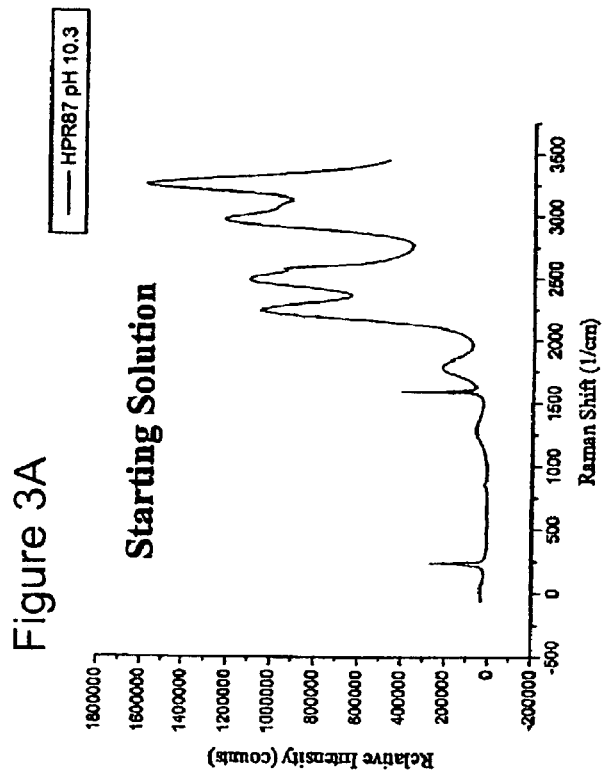
FIG. 3A shows a Raman spectrum of individually-suspended single-wall carbon nanotubes in a 1% $SDS/D_2O$ solution adjusted to pH 10.3.
Figure 3D:
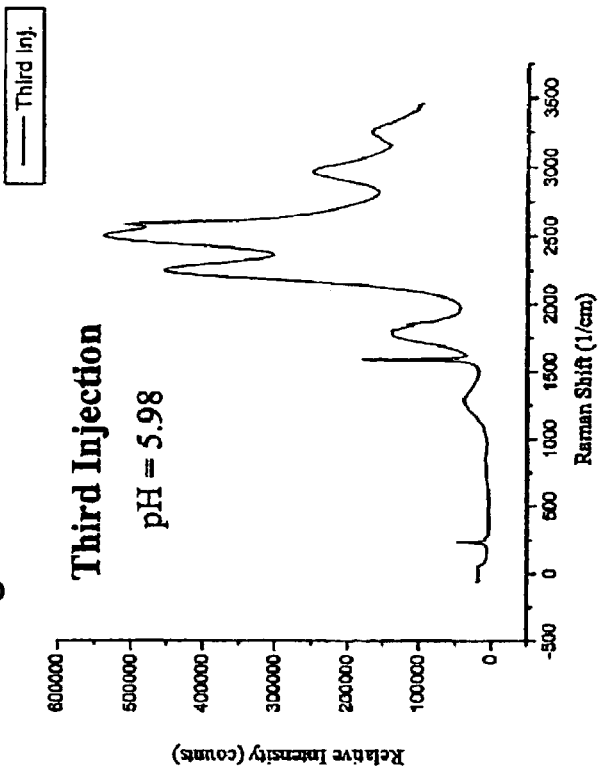
FIG. 3D shows a Raman spectrum of individually-suspended single-wall carbon nanotubes in a 1% $SDS/D_2O$ solution adjusted to pH 5.98.
Figure 3C:
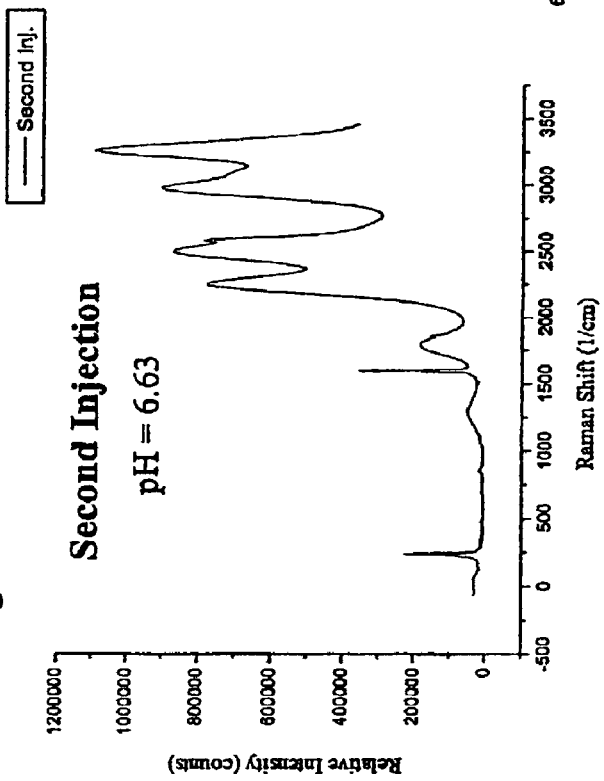
FIG. 3C shows a Raman spectrum of individually-suspended single-wall carbon nanotubes in a 1% $SDS/D_2O$ solution adjusted to pH 6.63.

This example demonstrates the effect of changing the pH of a suspension of single-wall carbon nanotubes in a 1 wt % sodium dodecyl sulfate (99.9%, Sigma-Aldrich) (SDS)/$D_2O$ (99.9%, Cambridge Isotope Lab.) solution. The surfactant suspended single-walled carbon nanotubes were monitored using Raman, absorption and fluorescence spectroscopy as the solution pH is lowered from about pH 10.3 down to about 3.8 and cycled back to pH 10. Aliquots of 1 N NaOH or HCl (Fisher Scientific) were added to equilibrate to the desired pH. Titrations were performed in an open, stirred three-necked 250 ml flask exposed to air. Equilibration was confirmed by monitoring transient changes in the tangential mode of the Raman spectrum. Raman spectroscopy was performed in-situ using a Kaiser Process Raman Spectrometer (Kaiser Optical Inc.) with 20 mW laser intensity focused on the solution in the flask. Excitation wavelengths of 532 and 785 nm were employed. A 1 ml sample of solution was removed from the flask at each equilibrated pH and the absorbance spectrum was recorded with a Shimadzu UV3101 Scanning spectrophotometer. As the pH was lowered, Raman features, absorption and fluorescence decrease selectively. A series of Raman spectra are given in FIGS. 3A through 3G. Small band-gap semiconducting nanotubes are protonated first (see FIG. 3D) before larger band-gap, smaller diameter semiconducting nanotubes (see FIGS. 3E and 3F). With the addition of 0.1 N NaOH base to increase the pH back to 10.3 (see FIG. 3H), the sample appears restored to the initial non-protonated state, as shown in FIG. 3A. The absorbance spectra are shown in FIG. 4A where the absorption spectra are offset from pH 8 (line 405) by a constant value to show changes (pH 6, −0.1 (line 404); pH 5.4, −0.2 (line 403); pH 5.1, −0.3 (line 402); pH 2.5, −0.4 (line 401)). FIG. 4B shows a plot of absorbance as a function of pH for two particular semiconducting nanotubes, namely (13,3) and (10,2) nanotubes (lines 406 and 407, respectively).

EXAMPLE 3

This example demonstrates a method to separate a mixture of as-produced single-wall carbon nanotubes by type using selective charge transfer and capillary electrophoresis. As-produced HIPCO® single-wall carbon nanotube material (produced by high temperature, high pressure disproportionation of CO), was mixed with a solution of 1 wt % sodium dodecyl sulfate (SDS) anionic surfactant in water, ultrasonicated at 540 W and placed in an ultracentrifuge and rotated with a force of 122,000 g. The supernatant, containing a homogeneous mixture of a distribution of different types of individual single-wall carbon nanotubes, rather than as aggregated bundles, or "ropes," was decanted. The ionic strength of the decant was adjusted to about 70 mM using excess SDS surfactant. The nanotube-SDS solution was acidified to effect nanotube protonation by adding concentrated HCl. The pH after HCl addition was pH 3. The ionic strength of the nanotube sample was adjusted and placed in a solution containing controlled amounts of surfactant, electrolyte and counter-ions at the desired ionic strength.

A Tris buffer solution at pH 8 was prepared with Tris base ((Tris-hydroxymethyl) aminomethane) (Mol. Wt. 121.1) to have a nearly matching ionic strength (70 mM) of the nanotube/surfactant decant solution through the addition of excess SDS surfactant.

A sample of the acidified nanotube/SDS (pH 3) solution was injected into a fused silica capillary tube (75 micron inner diameter, 375 micron outer diameter, and 50 cm in length) by applying 0.5 psi pressure to the solution for 15 seconds to fill about 1.7 cm of the capillary with the sample. Each end of the capillary was placed in separate buffer reservoirs, i.e. vessels (about 2 ml in volume) each filled with the Tris buffer solution.

An electric field (not exceeding 120 V/cm) was applied across the capillary which was held at constant temperature 25° C. by thermostatic control. The field was applied by placing platinum-coated electrodes into each buffer reservoir at either end of the capillary. A positive (+) potential was applied at the inlet end and a negative (−) potential is applied at the outlet end of the capillary. The electric field was ramped from zero to the operating strength of 5 kV over a 2 minute period and held constant for about 2.5 hours.

The protonated nanotubes flowed towards the negatively-charged electrode by electro-osmotic flow. The nanotubes migrated at different rates in the electric field based on their electric charge. The nanotubes separated (based on type) as they migrated with the induced flow while simultaneously being retarded based on variation in net charge.

Figure 5:
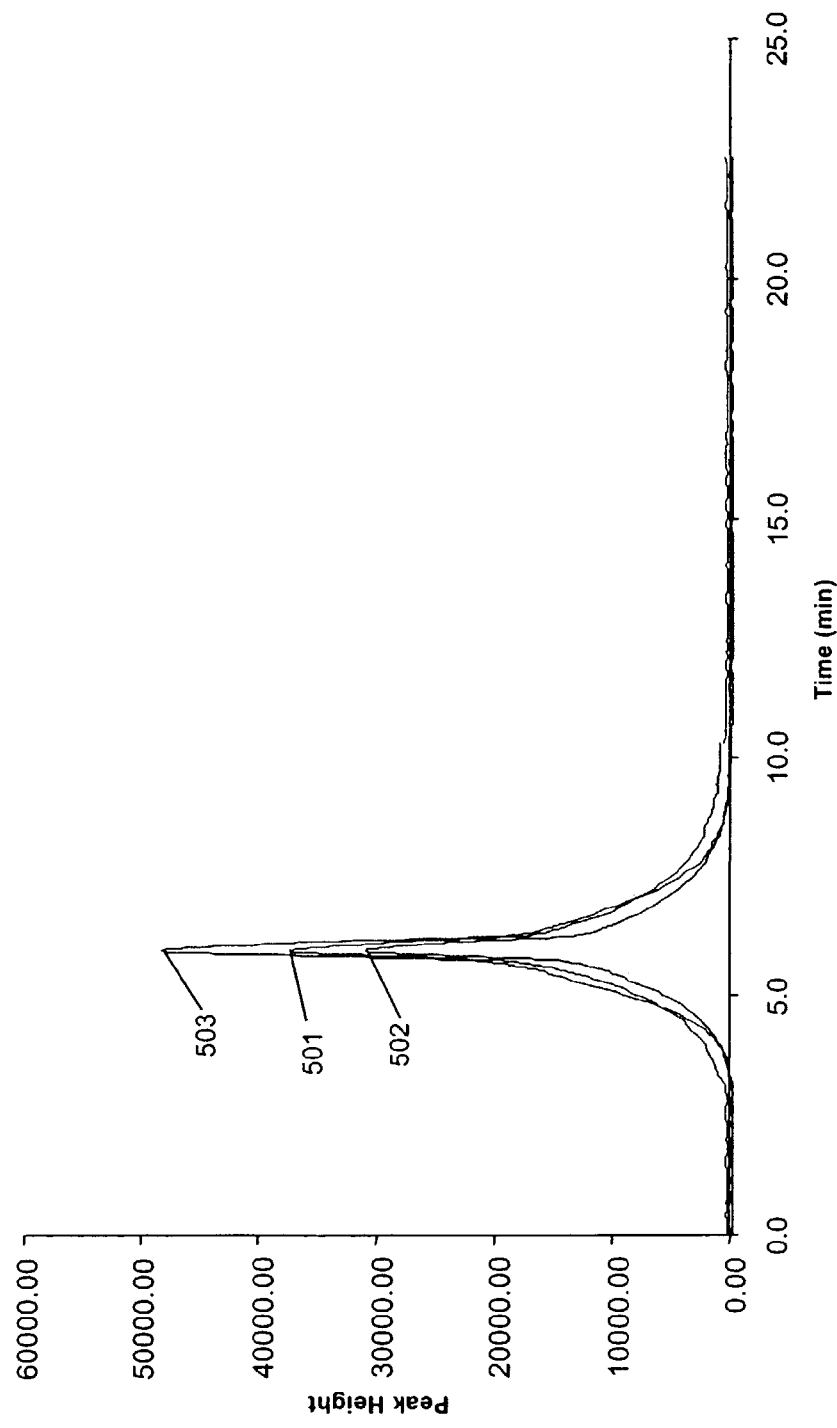
FIG. 5 shows Raman and near-IR peak monitoring for a sample of protonated single-wall carbon nanotubes at pH 3 during capillary electrophoresis without the application of an electric field.

Nanotube migration and separation were monitored by Raman scattering and near-IR fluorescence. Since only non-protonated semiconducting nanotubes will fluoresce, near-IR fluorescence can be observed for the semiconducting nanotubes until the pH is low enough to protonate them. FIGS. 5 through 9 show the evolution of the separation of nanotubes at pH 5 under the influence of the electric field at different elapsed times. In the absence of an electric field and only a pressure gradient, no nanotube sample separation was observed, such as shown in FIG. 5, where the sample migrated through the capillary as a single peak. (In FIG. 5, line 501 is the "G" peak; line 502 is the RBM") 233 $cm^{-1}$; and line 503 is the fluorescent features at 912 nm). FIG. 5 also shows that all Raman scattering features and fluorescence features are present in nearly constant ratios indicating negligible separation.

Figure 6:
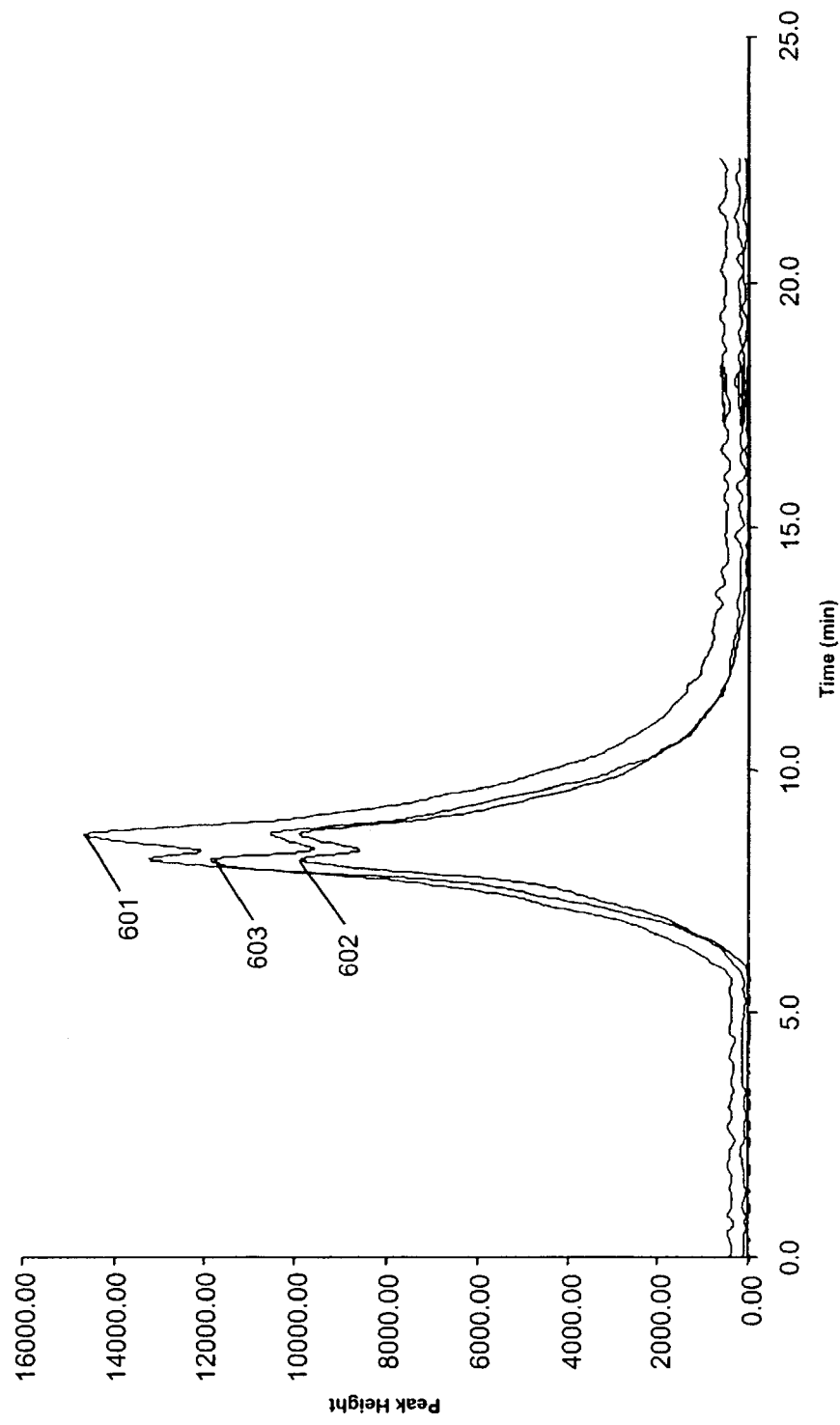
FIG. 6 shows Raman and near-IR peak monitoring for a sample of protonated single-wall carbon nanotubes at pH 3 during capillary electrophoresis with the application of an electric field ramped from 0 to 5 kV in 2 minutes.
Figure 7:
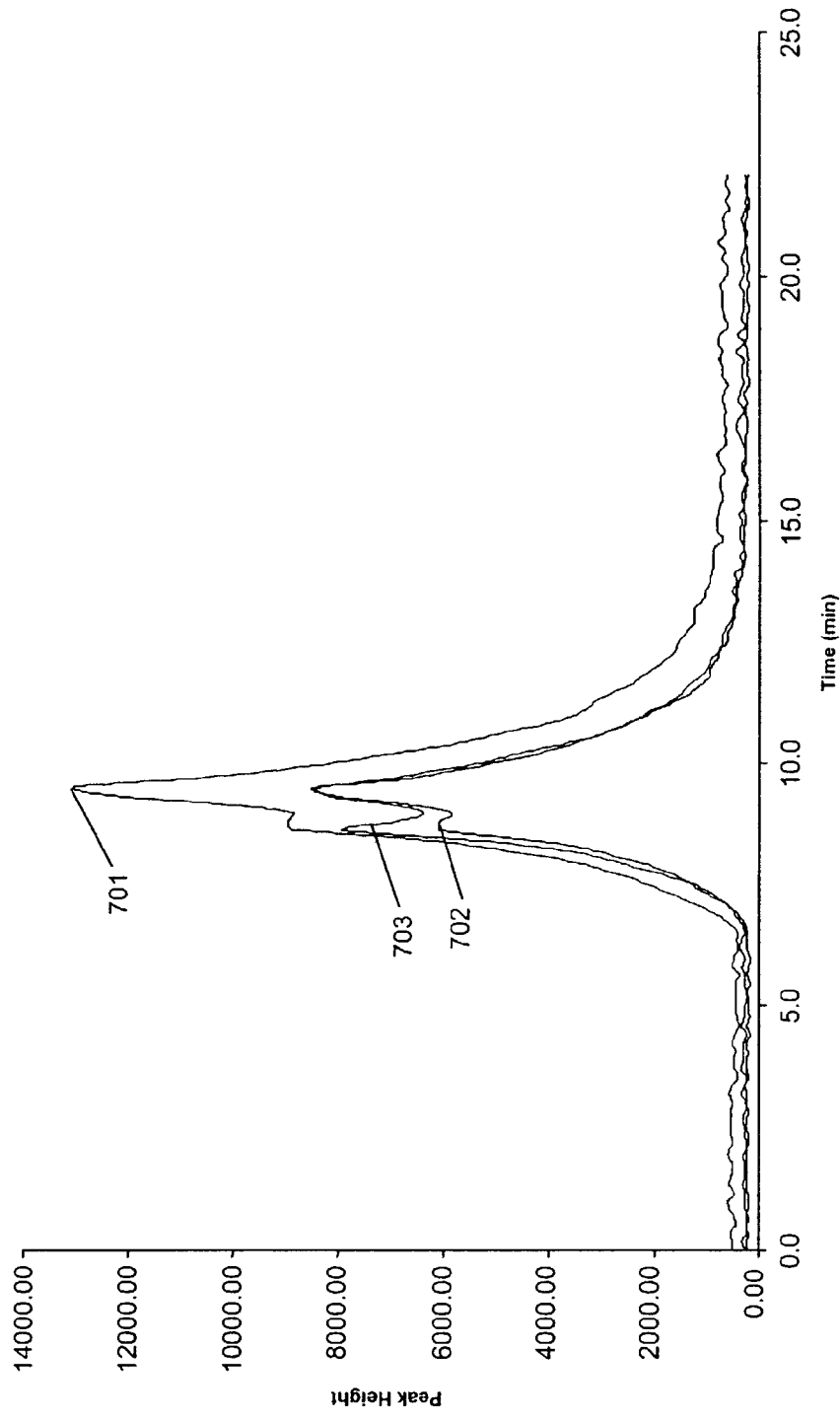
FIG. 7 shows Raman and near-IR peak monitoring for a sample of protonated single-wall carbon nanotubes at pH 3 during capillary electrophoresis with the application of an electric field ramped from 0 to 5 kV in 2 minutes and held at 5 kV for 1 minute.

FIG. 6 shows the result of applying an increasing electric field to the sample as a ramp from zero to 5 kV over 2 minutes and then expelling the sample using a pressure gradient. (In FIG. 6, line 601 is the "G" peak; line 602 is the RBM 233 $cm^{-1}$; and line 603 is the fluorescent features at 912 nm). The initial peak bifurcated into a bimodal distribution. Applying the electric field for 3 minutes further increased the separation, as shown in FIG. 7. (In FIG. 7, line 701 is the "G" peak; line 702 is the RBM 233 $cm^{-1}$; and line 703 is the fluorescent features at 912 nm).

Figure 8:
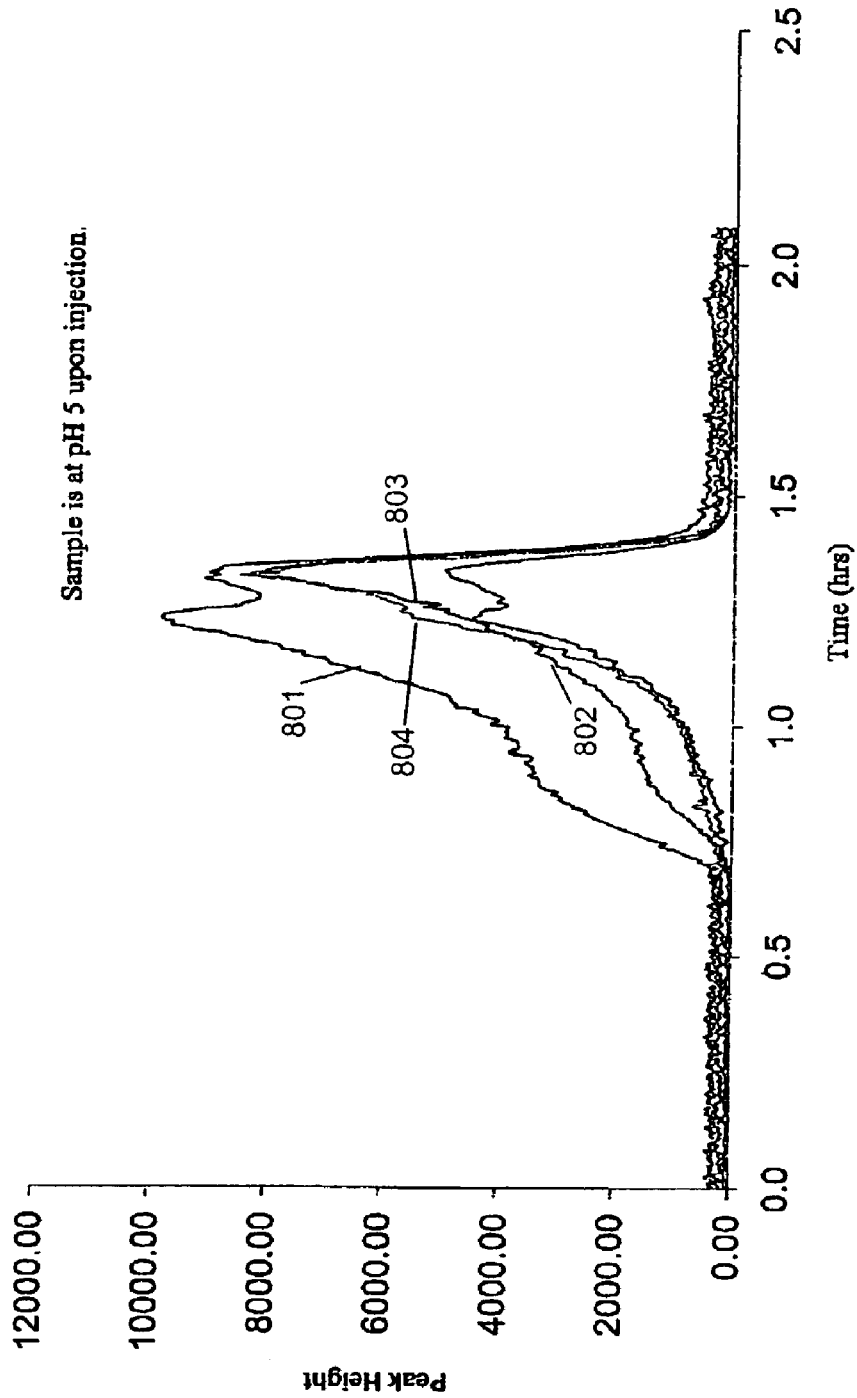
FIG. 8 shows Raman and near-IR peak monitoring for a sample of protonated single-wall carbon nanotubes at pH 5 during capillary electrophoresis with the application of an electric field ramped from 0 to 5 kV in 2 hours.
Figure 9:
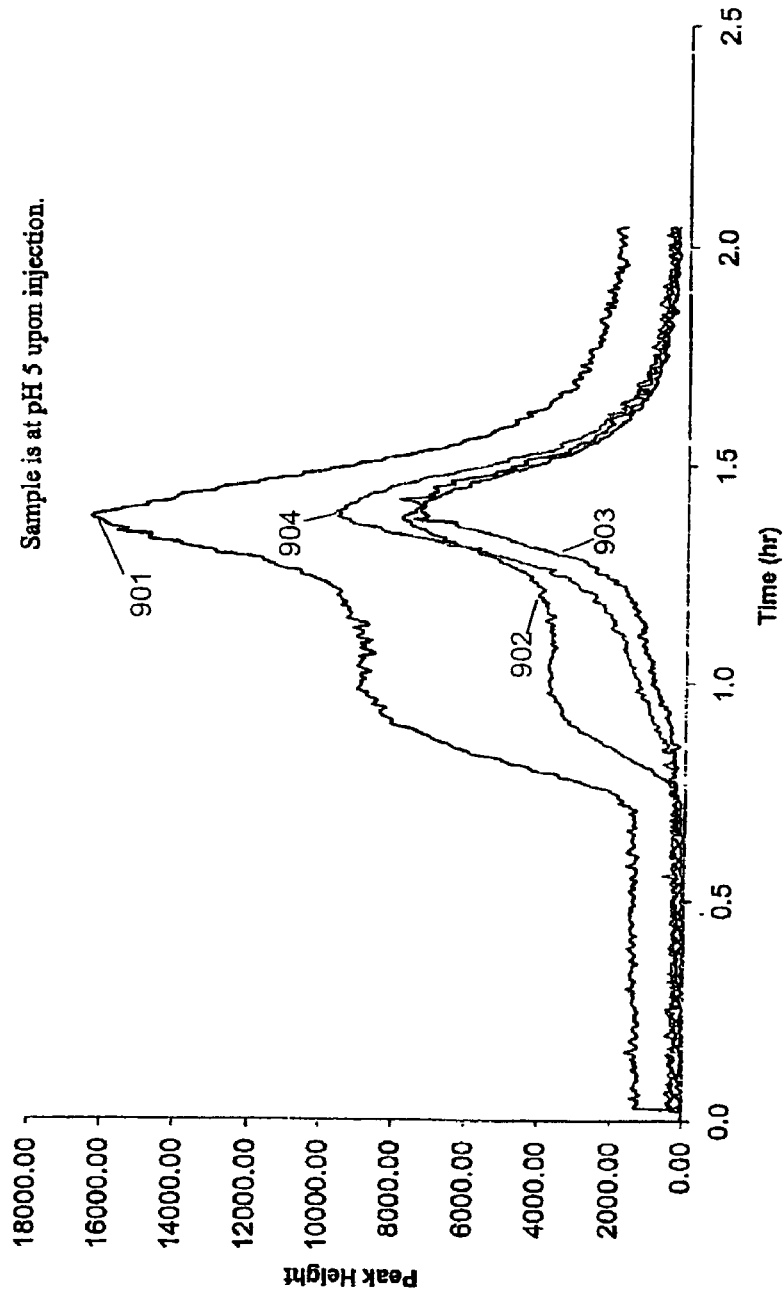
FIG. 9 shows Raman and near-IR peak monitoring for a sample of protonated single-wall carbon nanotubes at pH 5 during capillary electrophoresis with the application of an electric field ramped from 0 to 5 kV in 2 hours and without the application of a pressure gradient.

Application of the electric field for 2 hours with and without a pressure gradient, separated the sample into a bimodal distribution with the second concentrated fraction having a high quantum yield, as shown in FIGS. 8 and 9. FIG. 8 shows the separation at pH 5 with a pressure gradient. (In FIG. 8, line 801 is the "G" peak; line 802 is the RBM 233 $cm^{-1}$; line 803 is the fluorescent features at 912 nm, and line 804 is the fluorescent features at 870 nm). FIG. 9 shows the separation without a pressure gradient. The separation was reproducible and did not show evidence of nanotube aggregation. (In FIG. 9, line 901 is the "G" peak; line 902 is the RBM 233 $cm^{-1}$; line 903 is the fluorescent features at 912 nm, and line 904 is the fluorescent features at 870 nm).

Figure 10:
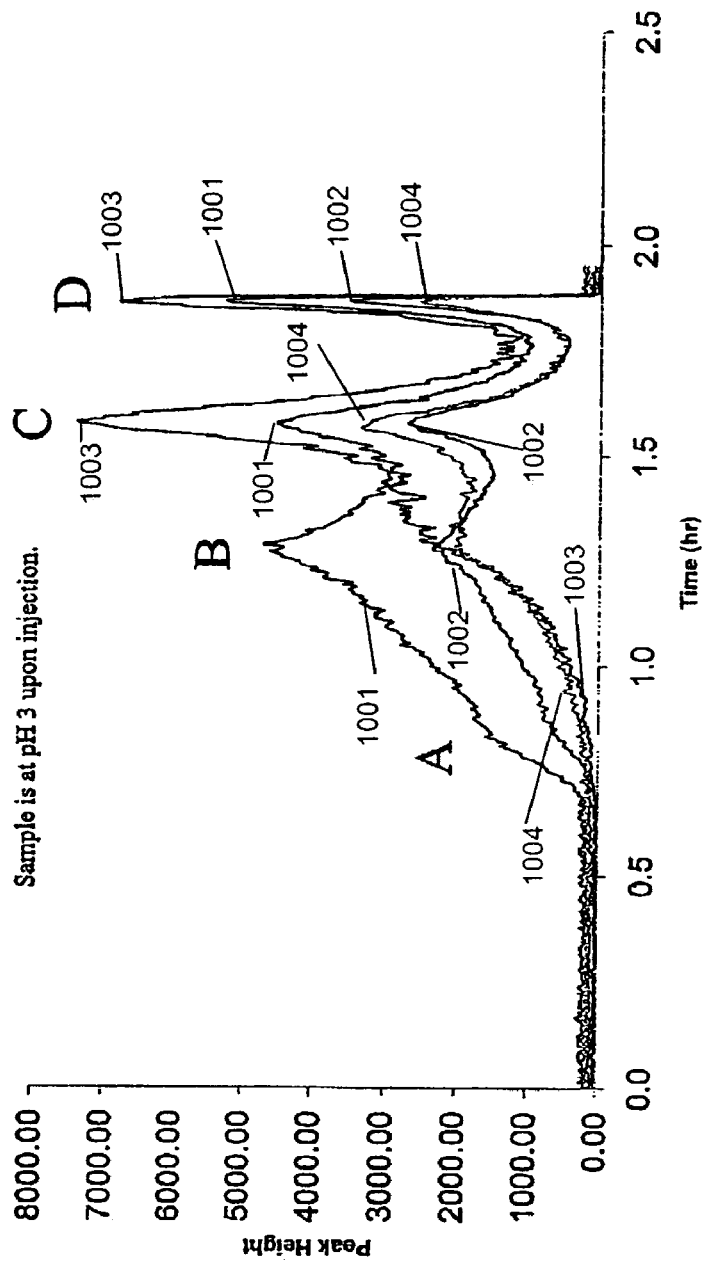
FIG. 10 shows Raman and near-IR peak fluorescence monitoring for a sample of protonated single-wall carbon nanotubes at pH 3 during capillary electrophoresis with the application of an electric field ramped from 0 to 5 kV for over 2 hours. "A," "B," "C," and "D" in the figure represent the migration time through the capillary, and are approximately 0.75 hours at point "A", 1.25 hours at point "B", 1.6 hours at point "C" and 1.8 hours at point "D."

Adjusting the pH of the nanotube suspension to pH 3 and subjecting the sample to an electric field, resulted in an even broader nanotube separation with three peaks. (See FIG. 10). FIG. 10 shows the separation of the nanotubes in terms of selected Raman and fluorescence peaks as a function of elution time. (In FIG. 10, line 1001 is the "G" peak; line 1002 is the RBM 233 $cm^{-1}$; line 1003 is the fluorescent features at 912 nm, and line 1004 is the fluorescent features at 870 nm$^{-1}$). The "A", "B", "C", and "D" labels on the profiles of FIG. 10 correspond to the approximate elution times of 0.75 hours, 1.25 hours, 1.6 hours and 1.8 hours, respectively.

Figure 11A:
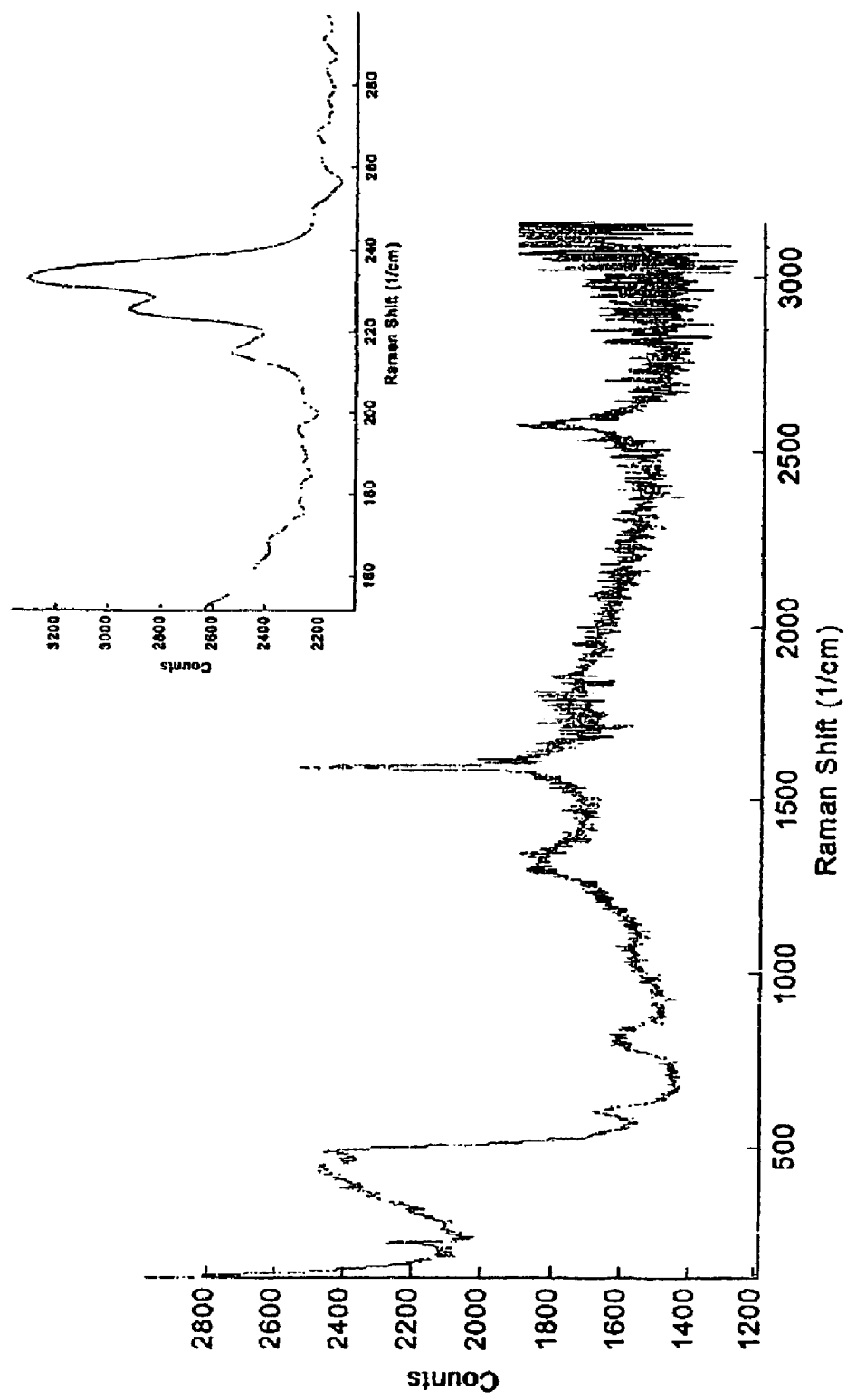
FIG. 11A shows Raman spectra for a sample of protonated single-wall carbon nanotubes that eluted from the capillary electrophoresis column at about 0.75 hours.
Figure 11B:
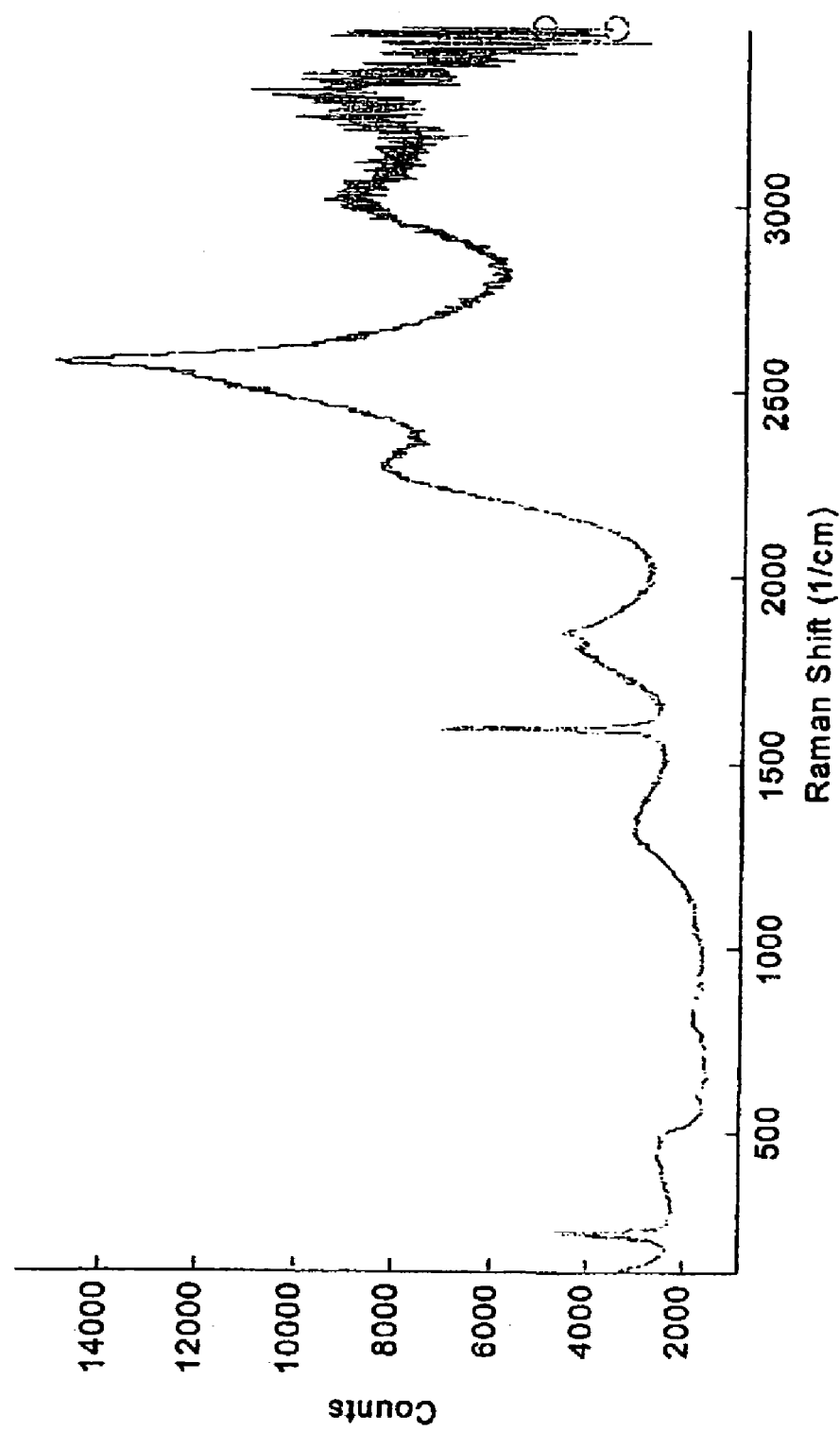
FIG. 11B shows Raman spectra for a sample of protonated single-wall carbon nanotubes that eluted from the capillary electrophoresis column at about 1.25 hours.
Figure 11C:
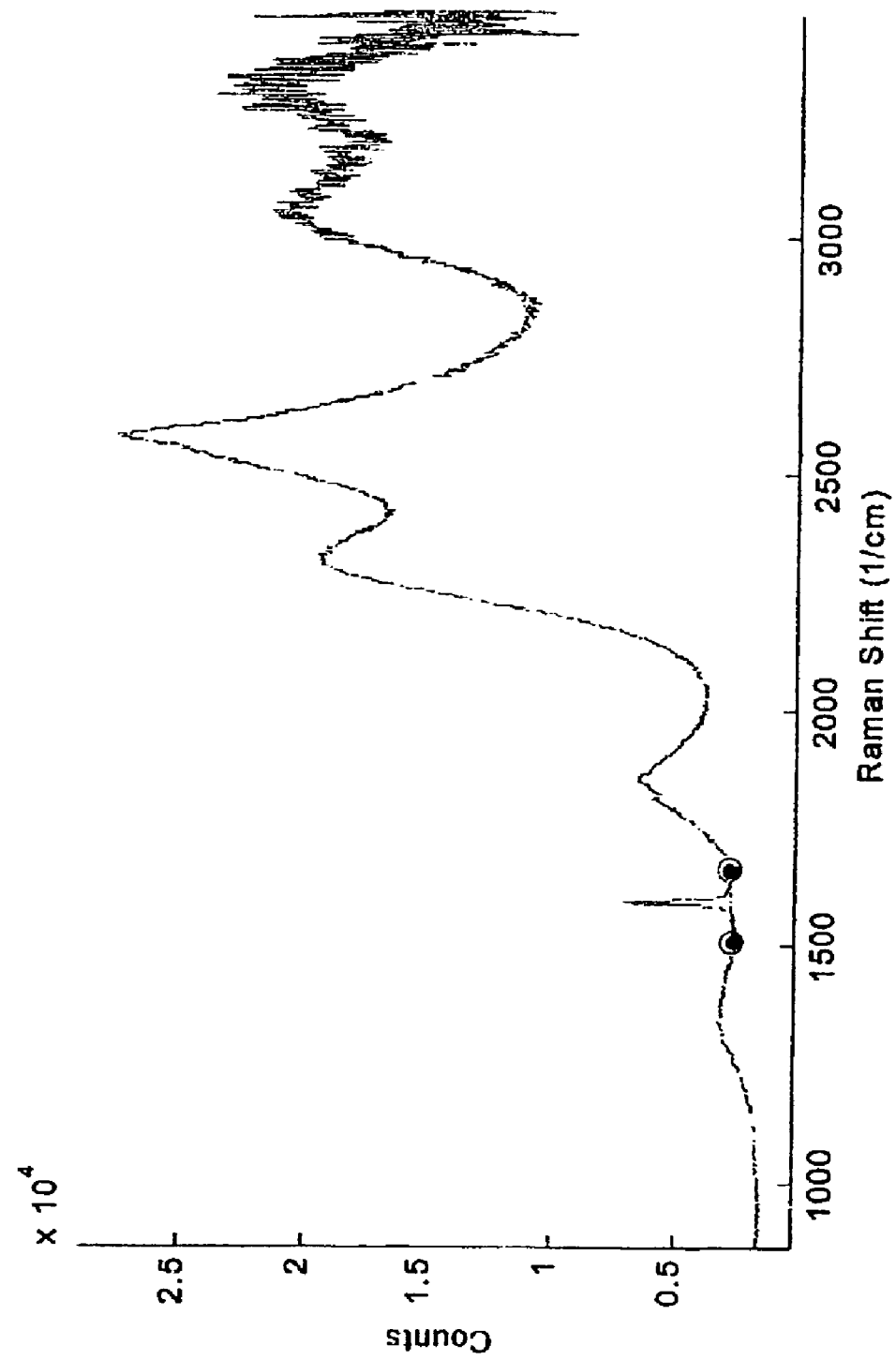
FIG. 11C shows Raman spectra for a sample of protonated single-wall carbon nanotubes that eluted from the capillary electrophoresis column at about 1.6 hours.
Figure 11D:
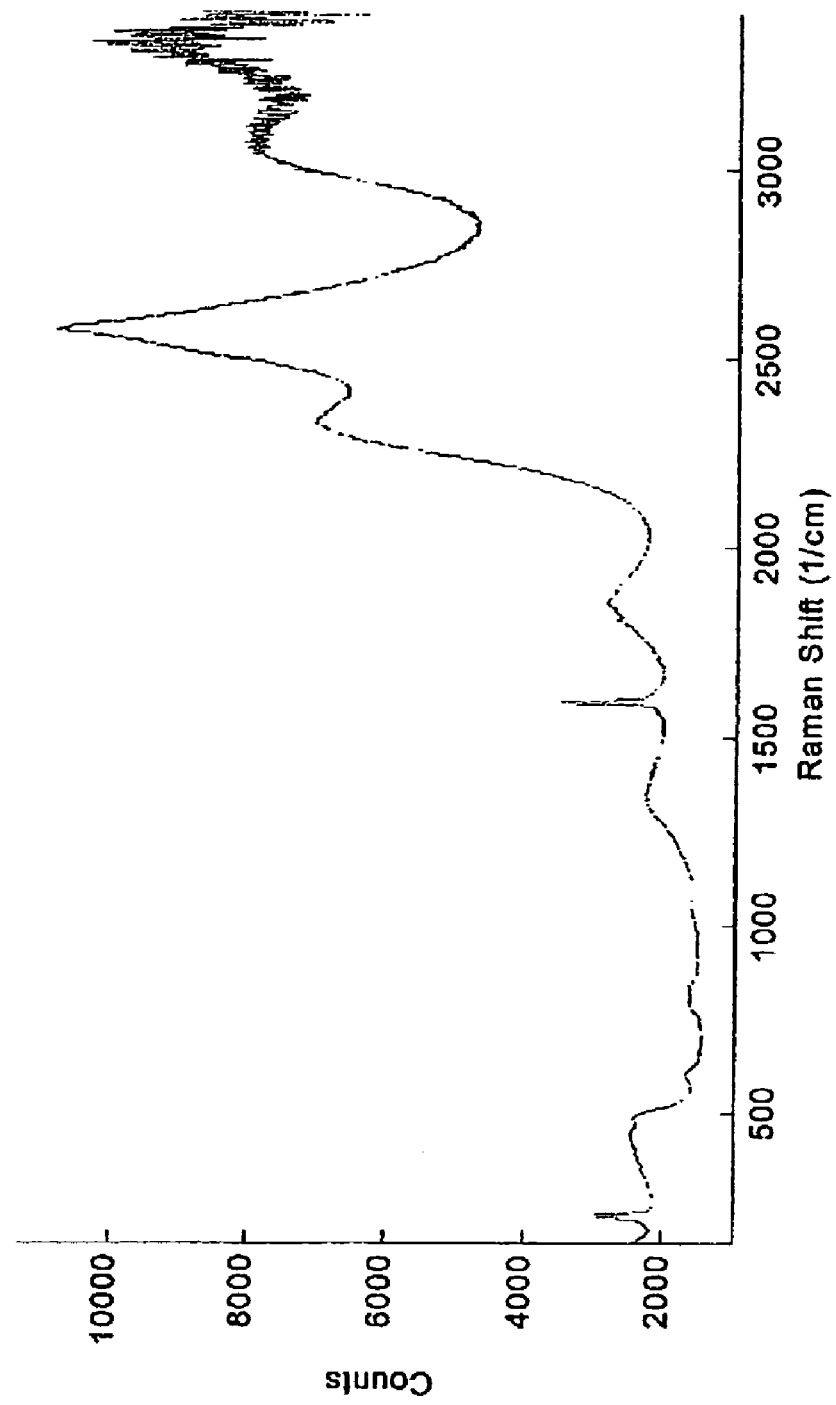
FIG. 11D shows Raman spectra for a sample of protonated single-wall carbon nanotubes that eluted from the capillary electrophoresis column at about 1.8 hours.
Figure 12A:
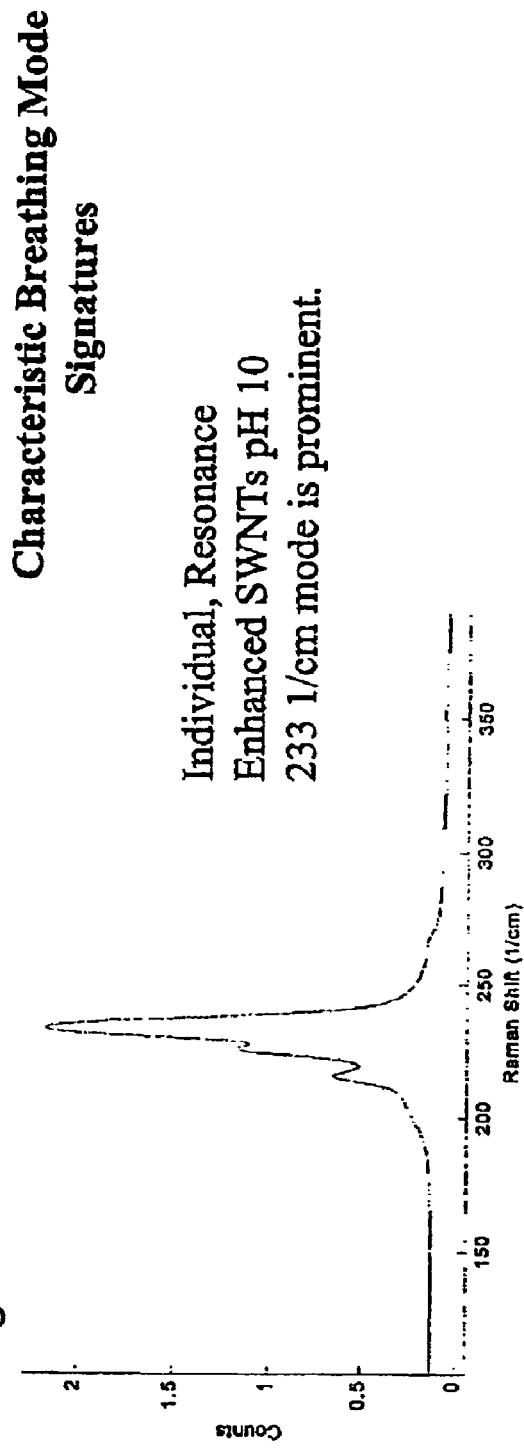
FIG. 12A shows Raman spectra (using a 785-nm laser wavelength) in the range of single-wall carbon nanotube radial breathing modes for individual-dispersed SWNT material at pH 10.
Figure 12B:
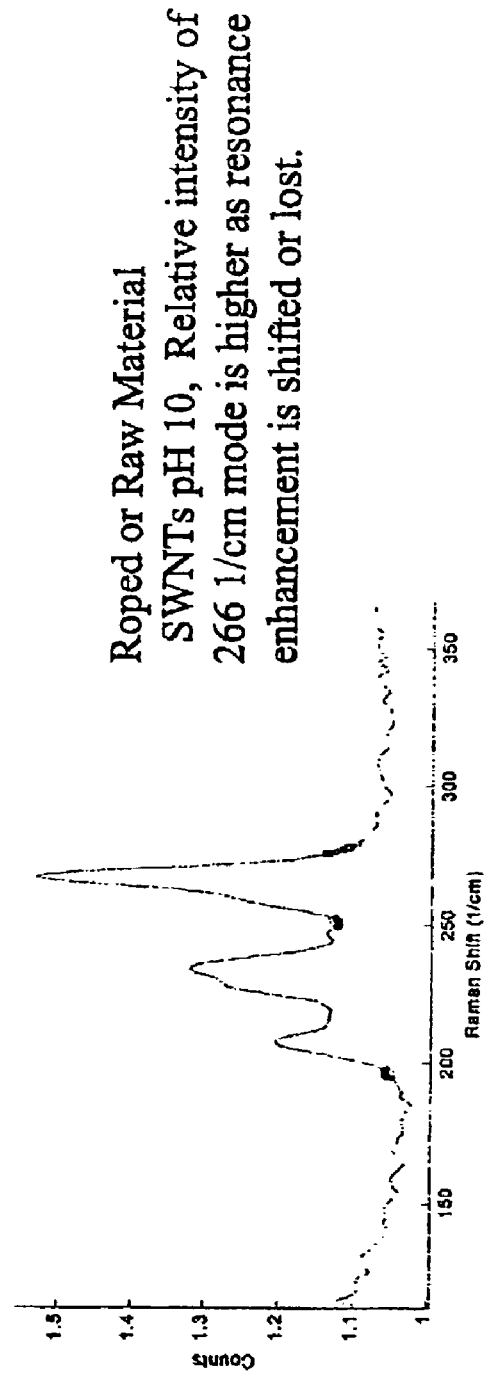
FIG. 12B shows Raman spectra (using a 785-nm laser wavelength) in the range of single-wall carbon nanotube radial breathing modes for roped or raw SWNT material at pH 10.

FIGS. 11A, 11B, 11C and 11D are Raman spectra that were taken at the same approximate elution times, i.e., 0.75 hours, 1.25 hours, 1.6 hours and 1.8 hours, respectively, and correspond to the "A", "B", "C", and "D" labels on the time axis of FIG. 10. FIG. 11A, taken at about 0.75 hours, shows that the early fractions are nanotube types that do not fluoresce, but show resonance-enhanced radial breathing mode peaks at 215, 225 and 233 cm$^{-1}$. FIGS. 12A and 12B shows Raman spectra (using a laser wavelength at 785 nm) of the characteristic breathing mode peaks for individually-dispersed and roped or raw single-wall carbon nanotubes, respectively. FIG. 12A shows the predominant 233 cm$^{-1}$ peak with individually-dispersed nanotubes. FIG. 12B shows that roped or aggregated nanotubes, which do not fluoresce, consistently show a dramatic loss of resonance enhancement of the peaks, 215, 225 and 233 cm$^{-1}$, relative to peak at 266 cm$^{-1}$ which becomes visible. The latter eluting fractions, shown in FIGS. 11B, 11C and 11D, show increased quantum yield of large band-gap semiconducting nanotubes as determined by fluorescence intensity. FIG. 10 at point C and FIG. 11C indicate a peak intensity ratio of fluorescence to the Raman tangential mode "G" peak at about 1590 cm$^{-1}$, that is much higher than any previous recorded for carbon nanotube samples.

EXAMPLE 4

Figure 13A:
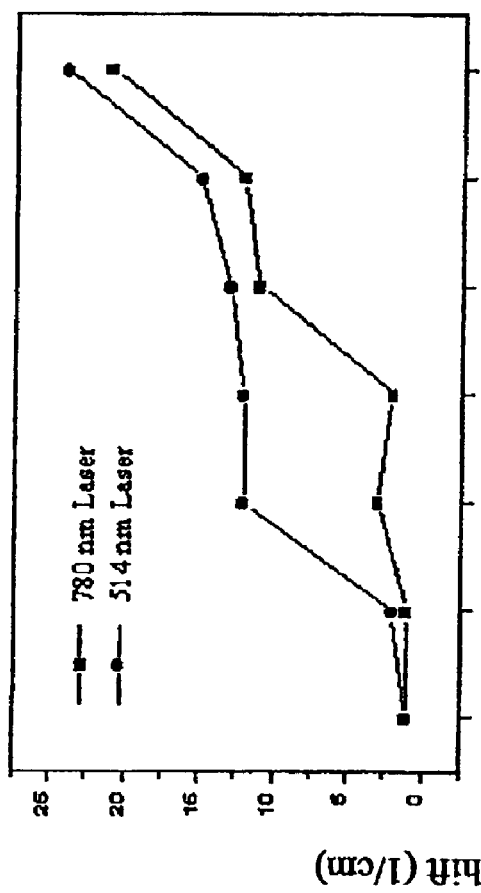
FIG. 13A shows Raman spectra upshifts in the tangential mode peak for laser oven-produced single-wall carbon nanotubes in the presence of different protonating acids.
Figure 13B:
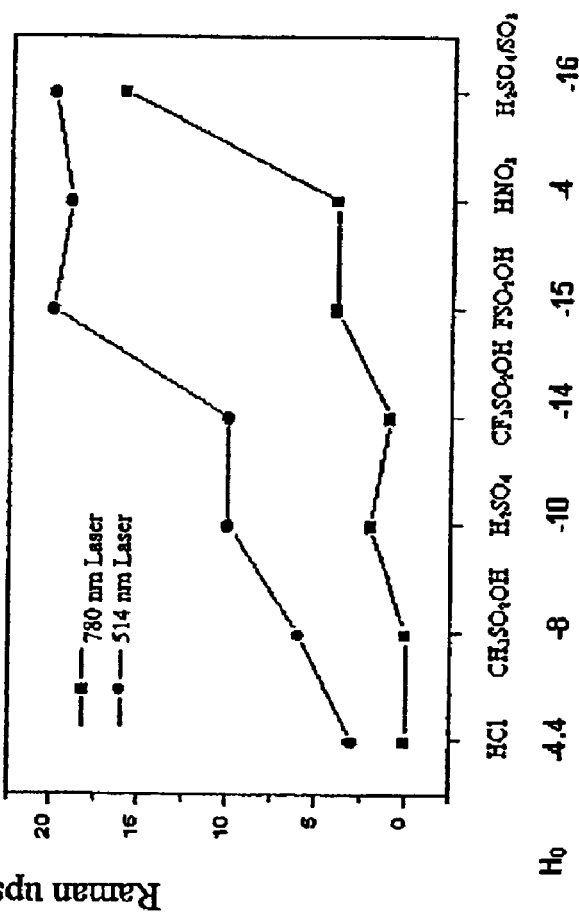
FIG. 13B shows Raman spectra upshifts in the tangential mode peak for HIPCO® single-wall carbon nanotubes in the presence of different protonating acids

This example demonstrates the separation of single-wall carbon nanotubes using preferential ionization of metallic nanotubes in a mixture of single-wall nanotube types using strong acids. Strong acids preferentially ionize metallic nanotubes and render them susceptible to electrophoretic type separations. Strong acids that can be used to preferentially ionize metallic single-wall carbon nanotubes include, but are not limited to, such acids as trifluoromethane sulfonic acid ($CF_3SO_3H$), concentrated sulfuric acid ($H_2SO_4$), hydrochloric acid (HCl), hydrofluoric acid (HF), nitric acid ($HNO_3$), fluorosulfuric acid ($FSO_3H$), chlorosulfonic acid ($ClSO_3H$), methane sulfonic acid ($CH_3SO_3H$), and oleum ($H_2SO_4/SO_3$). Either as-synthesized or purified single-wall carbon nanotube material can be treated with strong acid and the metallic nanotubes separated using a variety of different techniques including selective solvation of the metallic nanotubes in strong acids, electrodeposition from strong acids, and electromigration in strong acid media to yield high concentrations of metallic nanotubes separated from the semiconducting types. The effect is shown in FIGS. 13A and 13B plotting upshifts in the tangential mode Raman peaks for laser oven-produced SWNT material and HIPCO SWNT material (FIGS. 13A and 13B, respectively), using various acids.

EXAMPLE 5

This example demonstrates the change in fluorescence of semiconducting single-wall carbon nanotubes as a function of pH. A 1 wt % sodium dodecyl sulfate (SDS) in $D_2O$ was prepared. As-produced HIPCO® single-wall carbon nanotube material (Lot No. HPR45 produced by high temperature, high pressure disproportionation of CO at Rice University), was mixed with a solution of 1 wt % SDS/$D_2O$ such that the concentration of nanotubes was about 10 mg/l. The solution was ultrasonicated to suspend individual single-wall carbon nanotubes in surfactant micelles. The suspension was centrifuged to concentrate roped nanotubes, metallic impurities and other higher carbon forms in the sediment.

Figure 14A:
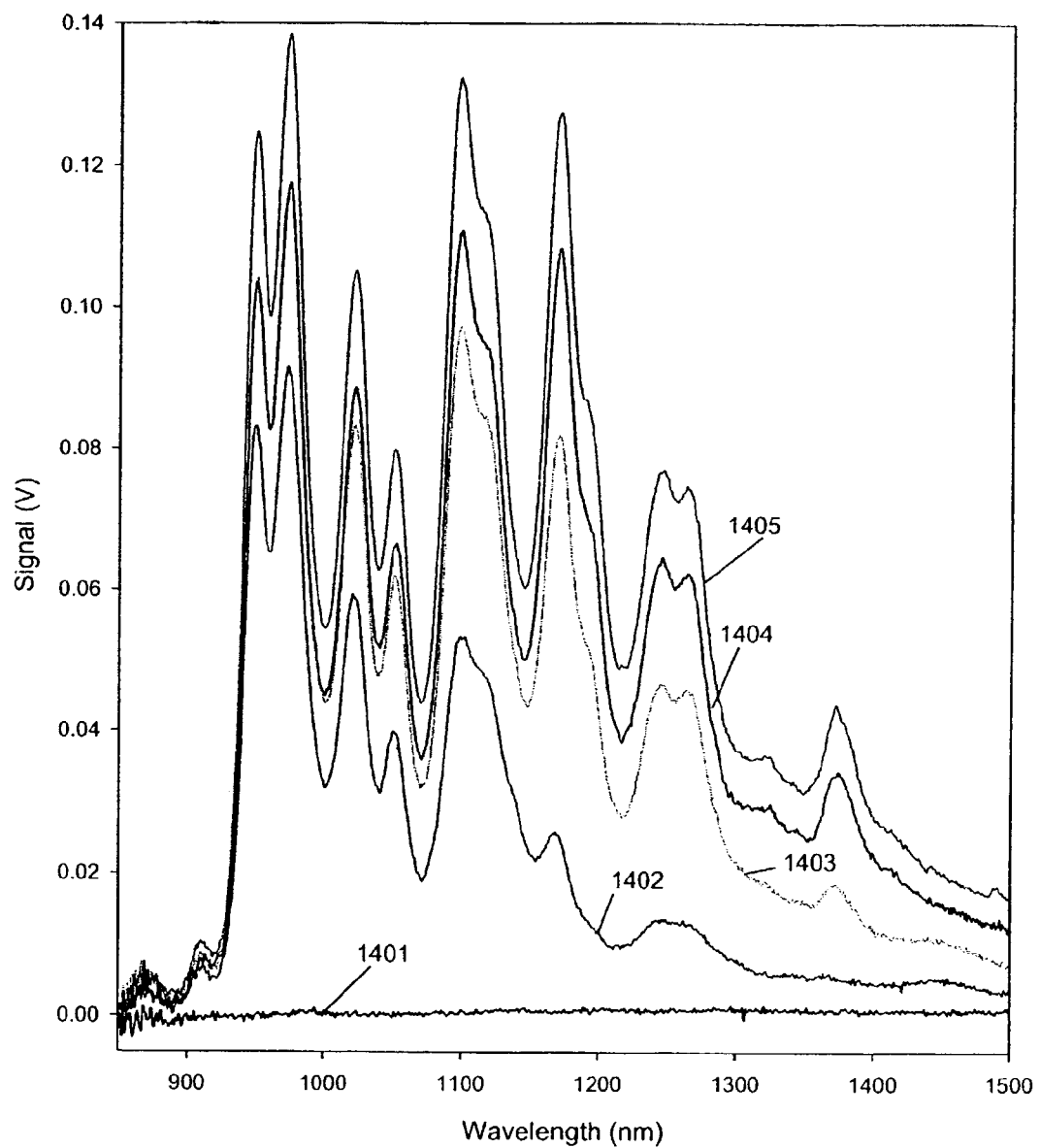
FIG. 14A shows fluorescence spectra from semiconducting single-wall carbon nanotubes excited at a wavelength of 350 nm as a function of pH.
Figure 14B:
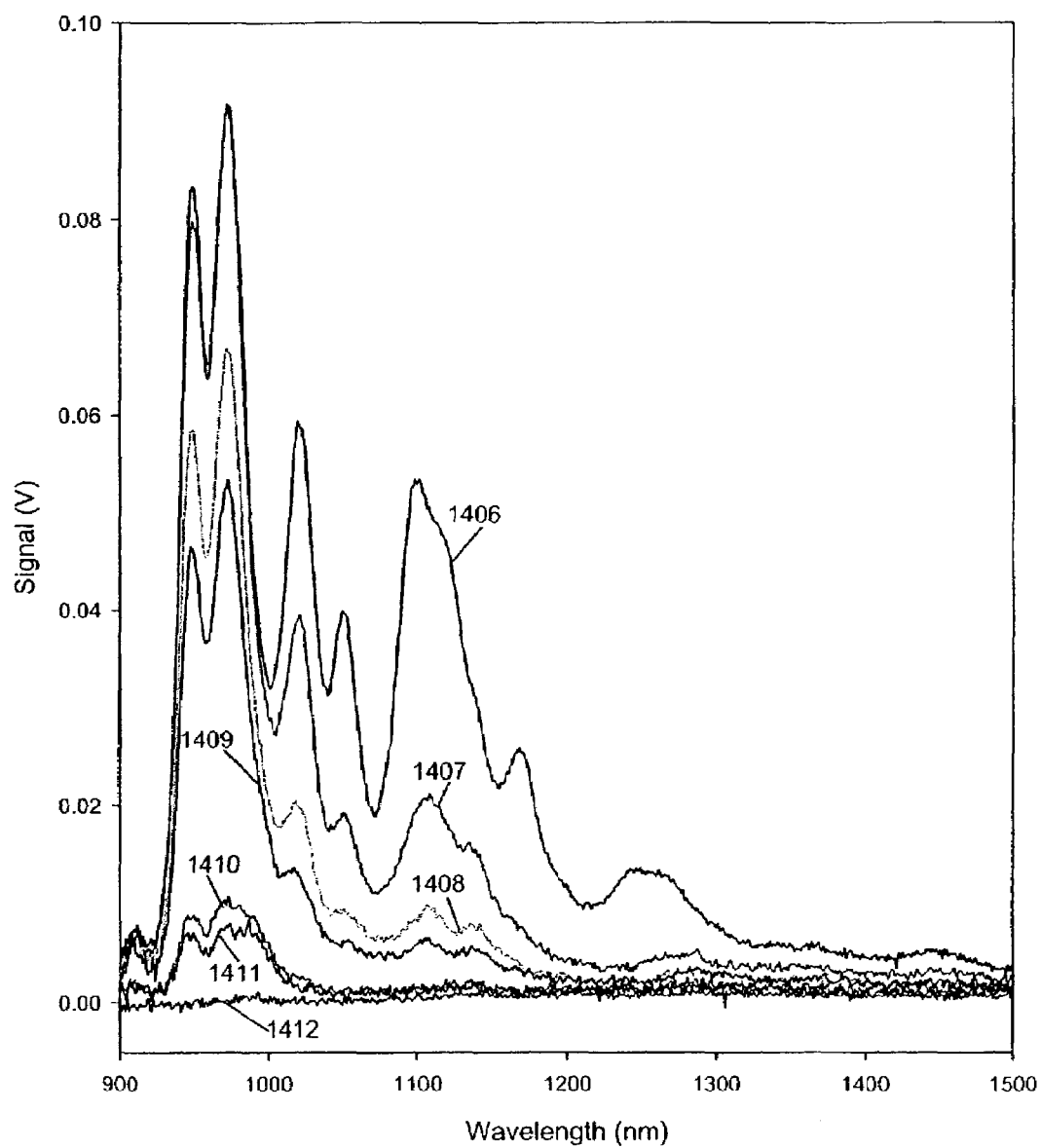
FIG. 14B shows fluorescence spectra from semiconducting single-wall carbon nanotubes excited at a wavelength of 350 nm as a function of pH.

The fluorescence spectra of the supernatant containing individually-suspended nanotubes were subject to excitation having a wavelength of 350 nm. The fluorescence spectrum of the suspension was collected at pH 7. The pH was lowered step-wise from pH 7 to pH 3 with $H_2SO_4$. The fluorescence spectrum collected again at each pH. A composite of all the spectra as a function of pH is given in FIG. 14A. (In FIG. 14, line 1401 is pH 3; line 1402 is pH 4; line 1403 is pH 5; line 1404 is pH 6; and line 1405 is pH 7). The fluorescence decreases with pH due to the progressive protonation of the semiconducting nanotubes. Not meant to be held by theory, the protonation of the semiconducting nanotubes progresses from higher pH to lower pH corresponding to protonation of the smallest band gap semiconducting nanotubes to the largest semiconducting nanotubes. At pH 3, all of the semiconducting nanotubes are protonated and no fluorescence signal is emitted. FIG. 14B shows the decrease in fluorescence intensity (see lines 1406–1412) as the pH is decreased from pH 4 (line 1406) to pH 3 (line 1412).

EXAMPLE 6

This example is a description of a SWNT sensor device for detecting dissolved carbon dioxide.

Individual carbon nanotubes refers to nanotubes processed in such a way that they can be made to fluoresce and yield sharp peaks in the photon absorption spectrum. They also have higher intensity Raman scatter upon laser excitation. To obtain these, raw, unprocessed HIPCO single-wall carbon nanotubes were produced by high pressure, high temperature iron catalyzed CO disproportionation. These were combined with 1 wt % sodium dodecyl sulfate (SDS) in heavy water ($D_2O$) to make a 200 mg/L nanotube solution. The solution was sonicated for 10 minutes, ultracentrifuged at 200,000 g for 2 hours and then the decant extracted. The nanotube suspension was adjusted to pH=10, using 0.1 N NaOH, and/or exposed to light and inert gas purge to remove quenching components from the nanotubes and obtain distinctive absorption features of the van Hove singularities, provide strong resonance Raman peaks, and strong fluorescence features in the near infrared. This process provides individually suspended nanotubes and minimizes quenching from either aggregation or adsorbed impurities.

The prepared nanotube suspension is placed in a closed glass container outfitted with a means for stirring or flowing the liquid. The gas to be detected is introduced into the container. Temperature, pressure, and flow rates are monitored with standard laboratory apparatus. A diode laser emitting red light in the range of 785 nm is transmitted by an optical fiber and focused with a lens through a glass surface into the vessel containing the carbon nanotubes in suspension.

The resultant fluorescence and Raman scattered light is collected by an optical lens and transmitted through optical fibers to a spectrometer. The scattered laser light is rejected by a filter means. The emitted light is dispersed and detected by a charge-coupled device (CCD) array detector. An InGaAs array detector is also suitable, as this has sensitivity that extends further into the infrared. The electronic signal from the detector is recorded by a computer, and this provides the intensity of the emitted light as a function of wavelength or frequency shift in the case of Raman scattering.

The spectrum shows a sequence of fluorescent features, or peaks, extending from 870 nm to about 1400 nm. Various diameter nanotubes emit various wavelengths, with the larger diameter nanotubes generally emitting longer wavelengths. When molecules adsorb onto the walls of the nanotube, these spectra features are altered. The longer wavelength features are generally altered first, as the concentration of the adsorbate molecules increases.

As with many molecular species, when carbon dioxide is present in the water, this alters the spectra being acquired. For lower concentrations, the longer wavelength emission derived from the larger nanotubes diminishes first, and is monotonically decreasing with increasing concentration. As the concentration increases, the longer wavelength fluorescence is extinguished. The shorter wavelength fluorescence from the smaller nanotubes then diminishes with increasingly high concentration. The signal intensities are compared to a reference spectrum for nanotube without the adsorbed gas. The concentration of the carbon dioxide adsorbate, or other gases or liquids, may then be determined. The fluorescence also shows a "red shift" to longer wavelengths that is sensitive to adsorbates, generally those with oxygen capable of electron donor-acceptor (EDA) bonding.

The spectra also have resonance Raman features. The low frequency shifts in the range of 200 to 370 $cm^{-1}$ correspond to the breathing modes, and the strongly resonant modes such as the radial breathing mode (RBM) feature at 234 $cm^{-1}$, are diminished considerably as the carbon dioxide concentration is increased. The "G-peak," around 1592 $cm^{-1}$, is also diminished, as is the two-phonon "G'-peak" mode around 2600 $cm^{-1}$. The disorder "D-peak" around 1300 $cm^{-1}$ tends to increase.

These SWNT sensing devices rely on disaggregated single-walled carbon nanotubes, which require special preparation. The micelle suspensions, or nanotubes wrapped with PVP or other polymers may tend to come out of suspension under some circumstances. For some free-floating sensor applications, it may be necessary to filter out the nanotubes in a subsequent step.

EXAMPLE 7

This example illustrates a nanotube-based sensor for pH using single-wall carbon nanotubes. Because of its small size, the nanotube tip sensor could be used as a nanoscale, interfacial sensor. The sensor comprises a fiber optic probe that irradiates 661-nm light and a surface of single-wall carbon nanotubes on the end of the probe. When the probe tip is placed into a solution for pH measurement, protons from solution interact with the nanotube tip. The excitation light induces fluorescence of the nanotube tip. Depending on the pH, some of the nanotubes will emit while others will not. The degree that each emit light is a direct function of the solution pH. The light travels up the shaft through a separate fiber optic to a near-IR (infrared) spectrometer that analyzes the collected light.

Specialized sensors using type-selected nanotubes could be made in the same way and detect selected pH limits, chemicals or conditions.

EXAMPLE 8

This example illustrates the use of single-wall carbon nanotubes to sense various molecules or molecular species, such as amines, ions, iodine, bromine, etc. A sensor could be constructed similar to that described in Example 6. Depending on the application and chemical moiety being detected, a shift in the emission peak could be monitored. For other applications, the decay of the emission and absorption peak could be monitored. The system is very robust in this way. Because of the probe's small size, interfacial sensing could also be done with these types of sensors. Concentration specific sensors could be made with type-selected nanotubes.

EXAMPLE 9

This example illustrates the use of single-wall carbon nanotubes to detect oxygen ($O_2$). A sensor could be constructed similar to that described in Example 6. In the case of an $O_2$ sensor, a laser could be directed through the barrel of the probe tip to clean off the nanotube tip before measurement. The probe could be placed in an enclosed membrane vessel with acidic solution. The nanotubes would fluoresce as long as no $O_2$ adsorbed on the surface, since the surface coverage of $O_2$ systematically reduces the emission. Thus, the amount of oxygen in solution can be measured. The probe could be made extremely narrow (even nanometer) in scale for interfacial applications and other space-limited applications.

EXAMPLE 10

This example illustrates the use of single-wall carbon nanotubes to detect malignant cells, such as, but not limited to, cancer cells, in a body. Single-wall carbon nanotubes are individually dispersed in a solution using non-covalent isolating moieties, such as bio-compatible polymers. Examples of biocompatible polymers include, but are not limited to, polymers and copolymers of polyethylene oxide and polypropylene oxide. The nanotubes are wrapped or coated in the biocompatible polymers and suspended in an aqueous media, such as water. Vigorous shear mixing and sonication is applied to the solution to individually suspend at least some of the nanotubes. The individually suspended nanotubes are then separated from bundled nanotubes and other carbonaceous and metallic matter by ultracentrifuging the mixture and decanting the supernatant. Individually-suspended nanotubes in the supernatant are reacted with a biological targeting moiety, such as a monoclonal antibody or other moiety that will attach to cancerous or other malignant cells.

The suspending media for the individual nanotubes that have been wrapped and "tagged" with a targeting moiety is either exchanged with a biocompatible fluid, such as a saline solution, or made compatible by the addition of one or more biocompatibilizing agents, in order for the wrapped and tagged nanotubes to be introduced into a biological living organism. Once in the body, the monoclonal antibody or other malignant cell-binding moiety migrate through the body and attach to target malignant cells. After time has elapsed for sufficient migration and attachment, the body is irradiated with appropriate excitation, preferably in the near-IR due to ability to penetrate tissue, for the selected nanotube type and simultaneously scanned for near-IR fluorescence emission. The location of the fluorescence is mapped and attributed to the location of the nanotubes with target moieties attached to the malignant cells. This sensor for malignant cells can be used on living organisms with minimal insult to the body.

EXAMPLE 11

This example illustrates the in vitro use of single-wall carbon nanotubes to detect and irradicate malignant cells, such as, but not limited to, cancer cells, in a body. Single-wall carbon nanotubes are prepared such as in Example 10, such that the nanotubes are in individually-suspended in a biocompatible solution and coated or wrapped with a generally non-perturbing biocompatible polymer. The individually-suspended nanotubes are separated from other nanotube bundles and impurities by centrifugation. The individually-suspended nanotubes in the decanted supernatant are reacted with a biological targeting moiety, such as a monoclonal antibody or other moiety that will attach to cancerous or other malignant cells.

The suspending media for the individual nanotubes that have been wrapped and "tagged" with a targeting moiety is either exchanged with a biocompatible fluid, such as a saline solution, or made compatible by the addition of one or more biocompatibilizing agents, in order for the wrapped and tagged nanotubes to be introduced into a biological living organism. Once in the body, the monoclonal antibody or other malignant cell-binding moiety migrate through the body and attach to target malignant cells. After time has elapsed for sufficient migration and attachment, the body is irradiated with appropriate excitation, preferably in the near-IR due to ability to penetrate tissue, for the selected nanotube type and simultaneously scanned for near-IR fluorescence emission. The location of the fluorescence, attributed to the nanotubes with target moieties attached to the malignant cells, can be mapped in a 3-D fashion.

Besides mapping the malignant cells, the malignant cells may be destroyed and irradicated by irradiating the nanotubes with a near-infrared laser that causes the nanotubes to absorb radiation and heat up. The localized heating of the nanotube, in contact with the malignant cell, causes the malignant cell to die by thermal necrosis. Raman spectroscopy can be used to monitor the local temperature of the nanotube.

In addition to "tagging" the nanotube with a targeting moiety, the nanotube can also be used as a vehicle for drug delivery. In this case, the nanotube tagged with a monoclonal antibody or other moiety designed to attach or congregate at malignant cell sites, also has an attached drug that is specific for the malignancy. When the nanotube is heated, the attached drug is designed to be liberated from the nanotube. Thus, the malignant cell is attacked and irradicated using both thermal and chemical processes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for separating a mixture of (n, m) single-wall carbon nanotubes into fractions based on the (n, m) types comprising:
    a) suspending a mixture of (n, m) single-wall carbon nanotubes in a liquid to form a suspension of individually-suspended nanotubes;
    b) adjusting the pH of the suspended nanotube mixture to cause protonation of a first fraction of x fractions of nanotubes, wherein x is an arbitrary whole number of at least 1;
    c) separating the suspended nanotube mixture by applying an electric field to the suspended nanotubes wherein the (n, m) single-wall carbon nanotube types migrate at different rates within the electric field, and wherein the different migration rates cause the protonated (n, m) single-wall carbon nanotubes to be separated by type;
    d) collecting by type the separated (n, m) single-wall carbon nanotubes.

2. The method of claim 1 further comprising:
    a) adjusting the pH of the suspended nanotube mixture to cause protonation of additional fractions of the remaining x−1 fractions of nanotubes;
    b) separating the suspended nanotube mixture for the remaining x−1 fractions of nanotubes; and
    c) collecting by type the separated (n, m) single-wall carbon nanotubes for the remaining x-1 fractions of nanotubes.

3. The method of claim 1 further comprising removing bundles of single-wall carbon nanotubes and non-nanotube material from the suspension of individually-suspended nanotubes.

4. The method of claim 3 wherein the removing is done by centrifuging the single-wall carbon nanotube mixture, wherein the bundles of single-wall carbon nanotubes and the non-nanotube material are concentrated in the sediment and removed, and wherein the individually-suspended nanotubes remain in suspension.

5. The method of claim 1 wherein the pH is adjusted with an acid.

6. The method of claim 5 wherein the acid is selected from the group consisting of hydrochloric acid, hydrofluoric acid, carbonic acid, sulfuric acid, nitric acid, chlorosulfonic acid, fluorosulfuric acid, methane sulfonic acid, trifluoromethane sulfonic acid, oleum and combinations thereof.

7. The method of claim 1 wherein the liquid comprises a surfactant and water.

8. The method of claim 7 wherein the surfactant is selected from the group consisting of anionic surfactant, cationic surfactant and nonionic surfactant.

9. The method of claim 7 wherein the surfactant is sodium dodecylsulfate.

10. The method of claim 7 wherein the surfactant forms a micellular structure around the individually-suspended nanotube.

11. The method of claim 1 wherein the liquid comprises a polymer and water.

12. The method of claim 11 wherein the polymer coats the individually-suspended nanotubes.

13. The method of claim 11 wherein the polymer is selected from the group consisting of: polyvinyl pyrrolidone (PVP), polystyrene sulfonate (PSS), poly(1-vinyl pyrrolidone-co-vinyl acetate) (PVP/VA), poly(1-vinyl pyrrolidone-co-acrylic acid), poly(1-vinyl pyrrolidone-co-dimethylaminoethyl methacrylate), polyvinyl sulfate, poly(sodium styrene sulfonic acid-co-maleic acid), polyethylene oxide (PEO), polypropylene oxide (PPO), dextran, dextran sulfate, bovine serum albumin (BSA), poly(methyl methacrylate-co-ethyl acrylate), polyvinyl alcohol, polyethylene glycol, polyallyl amine, copolymers thereof and mixtures thereof.

14. The method of claim 1 wherein the separating step is done by electrophoresis.

15. The method of claim 14 where in the electrophoresis method is selected from the group consisting of capillary electrophoresis, gel electrophoresis, paper electrophoresis and a combination thereof.

16. The method of claim 1 wherein the separating step is done by capillary electrophoresis.

17. The method of claim 1 wherein the (n, m) nanotube mixture is separated into at least two types of single-wall carbon nanotubes, wherein the first type comprises metallic (n, m) nanotubes and the second type comprises semiconducting (n, m) nanotubes.

18. The method of claim 1 wherein the adjusting step causes the pH to be lower.

19. The method of claim 1 further comprising deprotonating the separated protonated nanotubes.

20. The method of claim 19 wherein the deprotonation is done by increasing the pH to greater than the pH wherein the separated nanotubes were protonated.

21. A method for separating a mixture of (n, m) single-wall carbon nanotubes into fractions based on the (n, m) types comprising:
    a) suspending a mixture of (n, m) single-wall carbon nanotubes in a liquid to form a suspension of individually-suspended nanotubes;
    b) adjusting the ionic strength of the suspended nanotube mixture to cause a first fraction of x fractions of nanotubes to carry a charge, wherein x is an arbitrary whole number of at least 1;
    c) separating the suspended nanotube mixture wherein the charged-carrying (n, m) single-wall carbon nanotube types migrate at different rates, and wherein the different migration rates cause the charged (n, m) single-wall carbon nanotubes to be separated from each other; and
    d) collecting the separated (n, m) single-wall carbon nanotube types and the fraction of nanotubes that were uncharged.

22. The method of claim 21 further comprising repeating steps b), c) and d) with the uncharged fraction of the nanotube mixture x–1 times, wherein the x fractions of (n, m) nanotubes are charged and collected.

23. The method of claim 21 further comprising removing bundles of single-wall carbon nanotubes and non-nanotube material from the suspension of individually-suspended nanotubes.

24. The method of claim 23 wherein the removing is done by centrifuging the single-wall carbon nanotube mixture, wherein the bundles of single-wall carbon nanotubes and the non-nanotube material are concentrated in the sediment and removed, and wherein the individually-suspended nanotubes remain in suspension.

25. The method of claim 21 wherein the charge is imparted by a species selected from the group consisting of proton ($H^+$), hydronium ion ($H_3O^+$), and combinations thereof.

26. The method of claim 21 wherein the charge is imparted by an acid capable of protonating the individually-suspended nanotubes.

27. The method of claim 26 wherein the acid is selected from the group consisting of hydrochloric acid, hydrofluoric acid, chlorosulfonic, carbonic acid, sulfuric acid, nitric acid, fluorosulfuric acid, chlorosulfonic acid, methane sulfonic acid, trifluoromethane sulfonic acid, oleum and combinations thereof.

28. The method of claim 26 wherein the acid is selected from the group consisting of hydrochloric acid, sulfuric acid, nitric acid, oleum and combinations thereof.

29. The method of claim 21 wherein the liquid comprises a surfactant and water.

30. The method of claim 29 wherein the surfactant is selected from the group consisting of anionic surfactant, cationic surfactant and nonionic surfactant.

31. The method of claim 30 wherein the anionic surfactant is selected from the group consisting of N-lauroylsarcosine sodium salt, N-dodecanoyl-N-methylglycine sodium salt and sodium N-dodecanoyl-N-methylglycinate, polystyrene sulfonate, sodium dodecyl sulfate, sodium dodecyl sulfonate, sodium alkyl allyl sulfosuccinate and combinations thereof.

32. The method of claim 30 wherein the cationic surfactant is selected from the group consisting of dodecyltrimethylammonium bromide, cetyltrimethylammonium bromide, cetyltrimethylammonium chloride and combinations thereof.

33. The method of claim 30 wherein the nonionic surfactant is selected from the group consisting of N-lauroylsarcosine, N-dodecanoyl-N-methylglycine, polyethylene glycol dodecyl ether, polyethylene glycol lauryl ether, polyethylene glycol hexadecyl ether, polyethylene glycol stearyl ether, polyethylene glycol oleyl ether, block copolymers of polyethylene and polypropylene glycol, alkylaryl polyethether alcohols, ethoxylated propoxylated $C_8$–$C_{10}$ alcohols, t-octylphenoxypolyethoxyethanol, polyethylene glycol tert-octylphenyl ether, polyoxyethylene isooctylcyclohexyl ether, polyethylene glycol sorbitan monolaurate, polyoxyethylene monostearate, polyoxyethylenesorbitan tristearate, polyoxyethylenesorbitan monooleate, polyoxyethylenesorbitan trioleate, and polyoxyethylenesorbitan monopalmitate, polyvinylpyrrolidone, and combinations thereof.

34. The method of claim 29 wherein the surfactant is sodium dodecyl sulfate.

35. The method of claim 29 wherein the surfactant is dodecyltrimethylammonium bromide.

36. The method of claim 29 wherein the surfactant is a selected from the group consisting of alkylaryl polyethether alcohols, ethoxylated propoxylated $C_8$–$C_{10}$ alcohols, t-octylphenoxypolyethoxyethanol, polyethylene glycol tert-octylphenyl ether, polyoxyethylene isooctylcyclohexyl ether, and combinations thereof.

37. The method of claim 29 wherein the surfactant forms a micellular structure around the individually-suspended nanotube.

38. The method of claim 29 wherein the liquid comprises a polymer and water.

39. The method of claim 38 wherein the polymer coats the individually-suspended nanotubes.

40. The method of claim 38 wherein the polymer is selected from the group consisting of: polyvinylpyrrolidone (PVP), polystyrene sulfonate (PSS), poly(1-vinyl pyrrolidone-co-vinyl acetate) (PVP/VA), poly(1-vinyl pyrrolidone-co-acrylic acid), poly(1-vinyl pyrrolidone-co-dimethylaminoethyl methacrylate), polyvinyl sulfate, poly(sodium styrene sulfonic acid-co-maleic acid), polyethylene oxide (PEO), polypropylene oxide (PPO), dextran, dextran sulfate, bovine serum albumin (BSA), poly(methyl methacrylate-co-ethyl acrylate), polyvinyl alcohol, polyethylene glycol, polyallyl amine, copolymers thereof and mixtures thereof.

41. The method of claim 21 further comprising removing aggregates or impurities from the suspension of individually-suspended nanotubes by a means based on differences in density.

42. The method of claim 41 wherein the aggregates and impurities are removed from the suspension of individually-suspended nanotubes by centrifugation.

43. The method of claim 21 wherein the separating step is done by chromatographic means in the presence of an electric field.

44. The method of claim 21 wherein the separating step is done by electrophoresis.

45. The method of claim 44 where in the electrophoresis method is selected from the group consisting of capillary electrophoresis, gel electrophoresis, paper electrophoresis and a combination thereof.

46. The method of claim 21 wherein the separating step is done by capillary electrophoresis.

47. The method of claim 21 wherein the (n, m) nanotube mixture is separated into at least two types of single-wall carbon nanotubes, wherein the first type comprises metallic (n, m) nanotubes and the second type comprises semiconducting (n, m) nanotubes.

48. The method of claim 21 wherein the adjusting step causes the ionic strength to be higher.

49. The method of claim 21 further comprising neutralizing the charged separated nanotubes.

50. A method of separating single-wall carbon nanotubes according to (n, m) type, comprising the steps of:
  a) dispersing a mixture of (n, m) type single-wall carbon nanotubes in a surfactant-containing suspending medium to form a suspension comprising individual single-wall carbon nanotubes encapsulated in surfactant micelles;
  b) acidifying the suspension to protonate metallic and small band gap nanotubes; and
  c) separating single-wall carbon nanotubes of individual (n, m) type based on the degree of their protonation.

51. The method of claim 50 wherein the surfactant is selected from the group consisting of cationic surfactants, anionic surfactants, neutral surfactants, and combinations thereof.

52. The method of claim 50, wherein the surfactant is sodium dodecyl sulfate.

53. The method of claim 50, wherein ultrasonication is used to facilitate the dispersing step.

54. The method of claim 50, wherein the acidifying step comprises a stepwise addition involving separation of protonated nanotubes after each stepwise acid addition.

55. The method of claim 50, wherein the acidifying step comprises by adding a non-oxidizing acid.

56. The method of claim 50, wherein the separation step comprises processing through a chromatographic column.

57. The method of claim 50, wherein the separation step comprises processing over a chromatographic plate.

58. The method of claim 50, wherein the separation step comprises separation in an electric field.

59. The method of claim 50, wherein the separation step comprises capillary electrophoresis.

60. The method of claim 50, wherein the separation step comprises gel electrophoresis.

61. The method of claim 50, further comprising identifying the individual (n, m) type of single-wall carbon nanotube using Raman spectroscopy.

62. The method of claim 50, further comprising identifying the individual (n, m) type of single-wall carbon nanotube using luminescence spectroscopy.

* * * * *